(12) United States Patent
Rise et al.

(10) Patent No.: US 6,227,203 B1
(45) Date of Patent: May 8, 2001

(54) TECHNIQUES FOR CONTROLLING ABNORMAL INVOLUNTARY MOVEMENTS BY BRAIN STIMULATION AND DRUG INFUSION

(75) Inventors: Mark T. Rise, Monticello, MN (US); Alim Benabid, Grenoble; Dominique Caparros-Lefebvre, Guadeloupe, both of (FR)

(73) Assignees: Medtronic, Inc., Minneapolis, MN (US); Inserm, Paris (FR)

( * ) Notice: Subject to any disclaimer, the term of this patent is extended or adjusted under 35 U.S.C. 154(b) by 0 days.

(21) Appl. No.: 09/150,088

(22) Filed: Sep. 9, 1998

Related U.S. Application Data

(60) Provisional application No. 60/074,505, filed on Feb. 12, 1998.

(51) Int. Cl.[7] .............................. A61B 19/00; A61N 1/00; A61N 1/08

(52) U.S. Cl. ........................... 128/898; 604/891.1; 607/3; 607/46

(58) Field of Search ..................... 128/898, 899; 607/1, 2, 3, 4, 46, 45; 604/891.1

(56) References Cited

U.S. PATENT DOCUMENTS

| | | | |
|---|---|---|---|
| 3,850,161 | 11/1974 | Liss | 128/2.1 |
| 4,146,029 | 3/1979 | Ellinwood, Jr. | 128/260 |
| 4,692,147 | 9/1987 | Duggan | 604/93 |
| 4,867,164 | 9/1989 | Zabara | 128/421 |
| 5,025,807 | 6/1991 | Zabara | 128/421 |
| 5,119,832 | 6/1992 | Xavier | 128/786 |
| 5,293,879 | 3/1994 | Vonk et al. | 128/782 |
| 5,423,877 | 6/1995 | Mackey | 607/117 |
| 5,458,631 | 10/1995 | Xavier | 607/117 |
| 5,711,316 | 1/1998 | Elsberry et al. . | |
| 5,713,923 | * 2/1998 | Ward et al. | 604/891.1 |
| 5,716,377 | 2/1998 | Rise et al. . | |
| 5,832,932 | 11/1998 | Elsberry et al. . | |
| 5,833,709 | 11/1998 | Rise et al. . | |
| 5,978,702 | 11/1999 | Ward et al. . | |
| 6,018,682 | 1/2000 | Rise . | |
| 6,094,598 | 7/2000 | Elsberry et al. . | |

FOREIGN PATENT DOCUMENTS 940116    1/1994   (WO) ............................... 7/912.463

OTHER PUBLICATIONS

Raymond D. Adams, M.A., M.D., Maurice Victor, M.D., "Principles of Neurology," 1977, 6 pages.

Jerome Engel, Jr., M.D., Ph. D., "Seizures and Epilepsy," 1989, 5 pages.

Ernst Niedermeyer, M.D., Fernando Lopes Da Silva, M.D., "Electroencephalography–Basic Principles, Clinical Applications, and Related Fields—Third Edition," 1993, 4 pages.

(List continued on next page.)

*Primary Examiner*—David J. Isabella
(74) *Attorney, Agent, or Firm*—Banner & Witcoff, Ltd.

(57) ABSTRACT

The present invention discloses techniques for controlling abnormal involuntary movement (AIM) disorders as experienced by persons with Parkinson's disease under high dosage of levodopa by electrical stimulation and/or drug infusion. The present invention utilizes an implantable signal generator and an electrode and/or an implantable pump and catheter. High electrical stimulation pulses and/or drug therapy is provided to predetermined portions of the brain to blocking neural activity in the Centremedian-Parafasicularis nucleus thereby reducing activity in the medial pallidal nucleus (GPi) which, in turn, reduces the AIM disorder. A sensor may be used to detect the symptoms resulting from the AIM disorder. A microprocessor or algorithm may then analyzes the output from the sensor to regulate the stimulation and/or drug therapy delivered to the brain.

36 Claims, 21 Drawing Sheets

OTHER PUBLICATIONS

A.R. Crossman, "Experimental Hemiballisumus in The Baboon Produced By Injectin of A Gamma–Aminobutyric Acid Antagonist Into The Basal Ganglia," *Neuroscience Letters*, 20 (1980) 369–372.

Graham, Robertson, Sambrook & Crossman, "Injection of Excitatory Amino Acid Antagonists Into The Medial Pallidal Segment of A 1–Methyl–4–Phenyl–1,2,3,6–Tetrahydropyridine (MPTP) Treated Primate Reverses Motor Symptoms of Parkinsonism", *Sciences*, vol. 47, pp. PL–91–PL–97.

Alexander, Crutcher, "Functional architecture of basal ganglia circuits: neural substrates of parallel processing," *TINS*, vol. 13. No. 7 (1990).

Laitinen, Bargenheim, Hariz "Leksell's posteroventral pallidotomy in the treatment of Parkinson's disease," *Neursurg*, 76 (1992).

Capparros, Blond, Vesmersch, Pecheux, Guieu, Petit, "Chronic Thalamic stimulation improves tremor and levodopa induced dyskinesias in Parkinso's desease," *Journal of Neurology*, (1993).

Blond, Dominique, Lefebyre, Parker, Assaker, Petit, Guieu, Chhristiaens, "Control of tremor and involuntary movement disorders by chronic stereotactic stimulatin of the ventral itermediate nucleus," *Neurosurg* 77:62, (1992).

Laine, Blond, Capparos "Nouvelles possibilities de traetement du tremblement parkinsonien et de quelques autres mouvements anormaux par stimulation du noyau ventral intermediaire du thalamus," *Bull Acad Natle Med*, (1992).

Godsey, Lydell, "Omitrode: A Simple Cannula for Chemical and Bipolar Elecrial Stimulation." Brief Communication, *Physiology and Behavior*, vol. 8 pp. 773–775 (1972).

Dill, Nickey, Little, "Dyskinesias in Rats Following Chemical Stimulation of the Neosriatum," *Texas Report on Biology and Medicin* vol. 26, No. 1, Spring 1968.

Bergman, Wichmann, DeLong, "Reversal of Experimental Parkinsonism by Lesions of the Sbuthalamic Nucleus," *Life Science*, Dept. of Neurology, vol. 249.

Andy "Thalamic Stimulation for Control of Movement Disorders," *Appl. Neurophysurgery*, (1985).

Horne, Bement, Hoffer, Gerhardt, "Multichannel semiconductor–based electrodes for in vivo electrochemical and electrophysiological studies in rat CNS," *Neuroscience Letters*, 120 (1990).

Alexander, Crutcher, Delong, "Basal ganglia–thalamocorical circuits: Parallel substrates for motor, oculomotor, "prefrontal" and "limbic" *functions*," Dept. of Neurology.

Limousine, Pollak, Benazzouz, Hoffman, Le Bas, Broussolle, Perret, Benabid, "Effect on parkinsonian signs and symptoms of bilateral subthalamic nucleus stimulation," *Dept. of Clinical & Biological Neurosciences*, (1995).

Andy, "Thalamic Stimulation for Control of Movement Disorders," *Dept. of Neurosurery*, (1983).

Benabid, Pollak, Gervason, Hoffman, Gao, Hommel, Perret, De Rougemont, "Long–Term suppression of tremor by chronic stimulation of the ventral intermediate thalamic nucleus," *The Lancet*, vol. 337, (1991).

\* cited by examiner

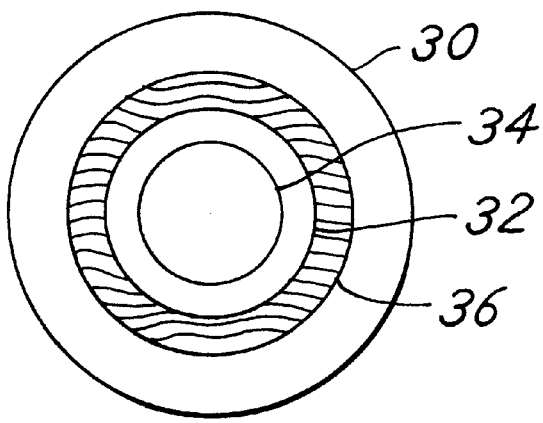
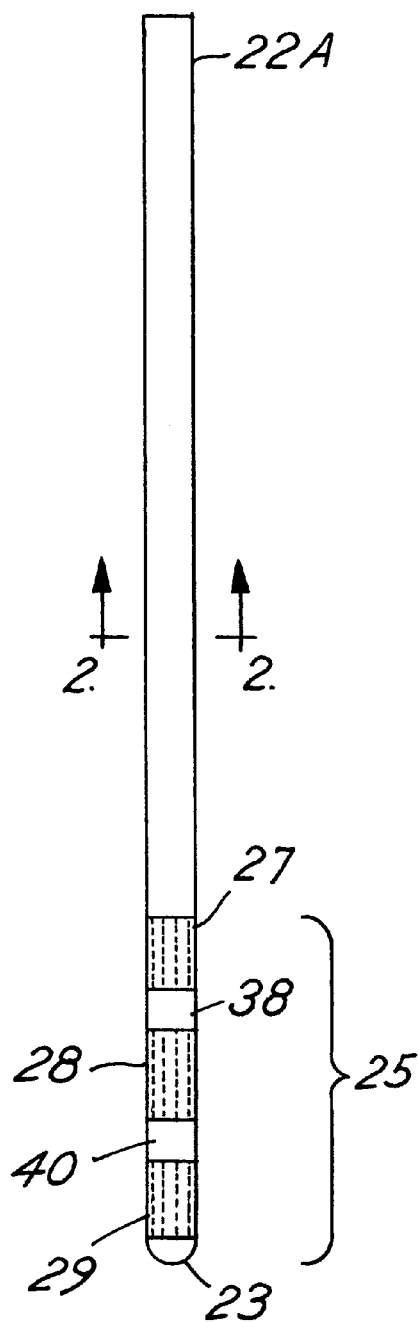

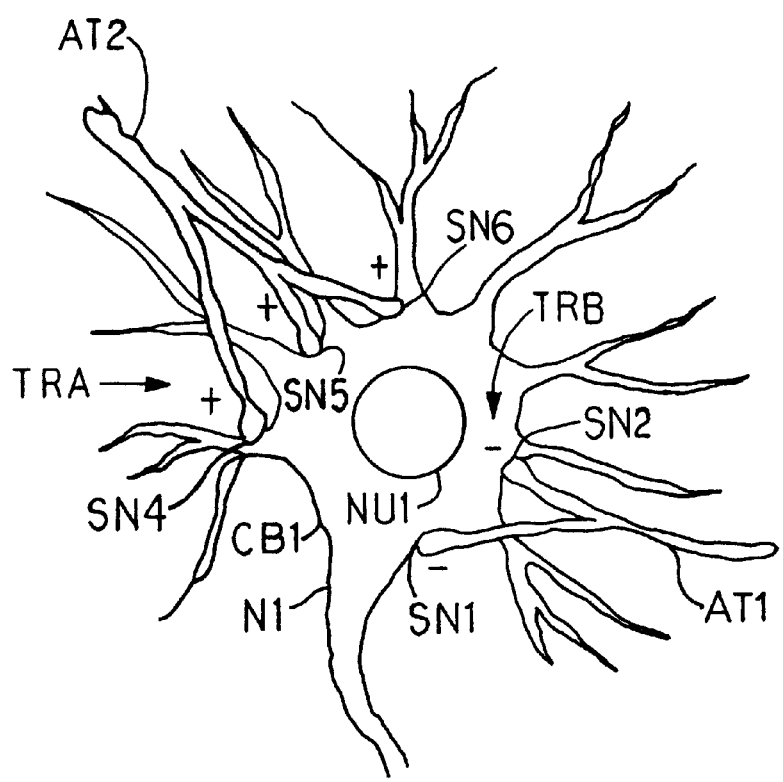
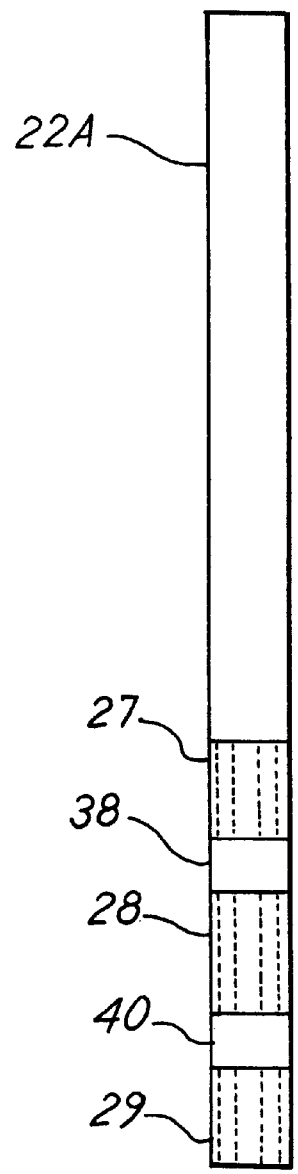
FIG.19

TECHNIQUES FOR CONTROLLING ABNORMAL INVOLUNTARY MOVEMENTS BY BRAIN STIMULATION AND DRUG INFUSION

BACKGROUND OF THE INVENTION

This is a continuation-in-part of Provisional Application Ser. No. 60/074,505 filed on Feb. 12, 1998 for which priority is claimed. This application is incorporated herewith by reference.

1. Field of the Invention

This invention relates to neural tissue stimulation and drug therapy techniques, and more particularly relates to such techniques for treating movement disorders.

2. Description of Related Art

Patients with neurodegenerative diseases or trauma like cerebral infarct or spinal cord injury can have a variety of movement and muscle control problems, like resting, postural, intention or action tremor, dystonia (improper muscle tone); spasticity (undesirable movements, or muscle co-construction); dyskinesia (poorly executed movements) or involuntary movements like ballismus, choreiform movements and torticollis (inappropriate movements or limb control). Many of these problems can be called hyperkinesia. Although they can be chronic, or worse, progressive, they also may have times of relative remission. Such problems are found, at certain stages, for patients with Parkinson's disease (PD), multiple sclerosis, cerebral palsy, secondary to deafferentation pain, post stroke, post apoplexy or anoxia, post head or spinal trauma, post poisoning, cerebellar disease, etc.

Specifically with regard to PD, levodopa treatment has traditionally been the main medical treatment for PD. A major iatrogenic complication of levodopa treatment, however, is abnormal involuntary movements (AIMs). AIMs generally occur in PD patients treated for a long time with high doses of levodopa. Levodopa is believed to induce a dysfunction of dopaminergic receptors located in striatal neurons. The striatal neurons therefore respond in a disharmonious mama, namely by switching abruptly from being unresponsive receptors (phase off) to being hyper-responsive receptors (phase on).

This "phase off" is mainly characterized by a major hypokinesia or akinesia, which tends to immobilize the patient in a frozen state. The "phase on" is mainly characterized by a rapid recovery from the unfrozen state, allowing the patient to resume activity. This recovery from the unfrozen state, however, is accompanied by involuntary abnormal movements, appearing at various moments following the intake of levodopa.

AIMs are extremely disabling and may constitute by themselves a symptom which has to be cured to improve the patient. Treatment specifically directed to treating AIMs includes for example pallidotomy. Laitinen L. V., Bergenheim A. T., Hariz M. I., Leksell's Posteroventral Pallidotomy in the Treatment of Parkinson's Disease, *J. Neurosurg.*, 76: 53–61, 1992. Although this technique, revived from that disclosed in Leksell Svenlinsonn et al., Treatment of Parkinsonism by Stereotactic Thermolesions in the Pallidal Region, A Clinical Evaluation of 81 Cases, *Acta Psychiatr. Neurol. Scand.*, 35, 358–377, 1960), is efficient on the contalateral side and partially efficient on the homolateral side, it is not applicable to bilateral symptoms which might require a bilateral procedure. Bilateral procedures are usually followed by serious side effects such as neuropsy-chological deficits. To prevent these side effects, high frequency stimulation of the internal pallidum (GPi) has been employed, leading to subsequent significant improvement or even disappearance of AIMs.

Neuroscientsts now have a better understanding of the neural connections hat make up the basal ganglia. These connections are reviewed in Alexander, Crutcher, and DeLong, "Basal ganglia-thalamocortical circuits: parallel substrates for motor, oculomotor, "prefrontal" and "limbic" functions. *Prog. Brain Res.* 85:119–146. The substantia nigra receives input from the subthalamic nucleus which is excitatory and involves glutamate as the neurotransmitter conveying information at the synapse. A lesion of the subthalamic nucleus will reduce the inhibitory output of the internal segment of the globus pallidus and substantia nigra reticulata. H. T. Bergman, T. Wichmann and M. R. DeLong, 1990, *Science,* 249:1436–1438.

Stimulation of the Vim nucleus of the Thalamus will block tremor. Benabid et al. *The Lancet*, Vol 337: Feb 16, 1991, 403–406. In this instance, stimulation at frequencies around 100 to 185 pulses per second accomplishes the same physiological response as a lesion of this region of the brain. Benabid's research team has extended this work to stimulation of the subthalamus in order to help reduce symptoms of motion disorders. "VIM and STN stimulation in Parkinson's disease", *Movement disorders*, Vol. 9, Supplement 1 (1994); "Effect on Parkinsonian signs and symptoms of bilateral subthalamic nucleus stimulation", *The Lancet*, Vol 345, Jan. 14, 1995.

Although stimulation of STN (subthalamic nucleus) and VIM (ventral intermediate thalamus) do not control or reduce AIMs, researchers have observed that AIMs may be controlled by stimulation of the GPi.

SUMMARY OF THE INVENTION

A preferred form of the invention can treat a movement disorder resulting in abnormal motor response by means of an implantable pump and an implantable catheter having a proximal end coupled to the pump and a discharge portion to deliver one or more drugs to a portion of the brain. The invention includes an implantable signal generator and an implantable electrode having a proximal end coupled to the signal generator and having a stimulation portion for therapeutically stimulating the brain. The cathode and electrode are implantable in the brain so that the respective discharge and stimulation portions lie within or in communication with predetermined portions of the brain sufficient to block activity of the CM-Pf complex of the thalamus. The pump is operated to deliver drug at a predetermined rate and dosage and the signal generator is operated to provide electrical stimulation at a predetermined pulse width, frequency and amplitude. With blocked or reduced activity of the CM-Pf complex of the thalamus, excitation of the GPi by the subthalamic nucleus is thereby reduced. The reduction in excitation of the GPi in turn reduces the occurrence of Abnormal Involuntary Movement (AIM) disorders. By using the foregoing method, the occurrences of AIMs in persons with PD is reduced.

Another form of the invention uses one or more drugs or electrical stimulation to treat AIM disorders. In this embodiment, only the signal generator/electrode or pump/catheter portion is required. Alternatively, drug treatment may be performed with the use of encapsulated cells selected to secrete the appropriate substance or a drug eluting polymer. These encapsulated cells may be implanted into a predetermined treatment site in brain tissue. In one embodiment of the invention stimulation and/or infusion is carried out in a nearly continuous manner. In another form of the invention, the stimulation or infusion is initiated by the patient in response to abnormal involuntary movements.

Another form of the invention uses a sensor in combination with the stimulation and/or infusion techniques discussed above to treat AIM disorders. In this form of the invention, the sensor generates a sensor signal relating to the extent of the AIM disorder. Control means responsive to the sensor signal regulate the signal generator so that the stimulation is increased in response to an increase in the AIM disorder and is decreased in response to a decrease in the AIM disorder. Control means may also regulate the infusion of medicaments to affect the AIM disorder.

BRIEF DESCRIPTION OF THE DRAWINGS

These and other advantages and features of the invention will become apparent upon reading the following detailed description and referring to the accompanying drawings in which like numbers refer to like parts throughout and in which:

FIG. 2 is a cross-sectional view of the catheter-electrode of FIG. 1 taken along line 2—2 of FIG. 3;

FIG. 3 is a diagrammatic view of the catheter-electrode shown in FIG. 1;

FIGS. 18–22 are diagrammatic views of the combined catheter-electrode shown in FIG. 1 arranged adjacent various types of neural tissue.

DESCRIPTION OF THE PREFERRED EMBODIMENTS

The present invention discloses techniques for blocking activity of the CM-Pf complex of the thalamus. The applicants have discovered that reduction in activity in the CM-Pf complex retrogradely inhibits the GPi nucleus. The reduction in excitation of the GPi in turn reduces the occurrence of Abnormal Involuntary Movement (AIM) disorders. The applicants have discovered that AIM disorders, can be treated by electrically simulating brain tissue either alone or while drugs are being administered as described above. Accordingly, the present invention incorporates electrical stimulation and/or drug infusion techniques to block activity of the CM-Pf complex. The catheter and/or electrode are implanted in the brain so that the infusion or stimulation portions lies within or in communication with predetermined portions of the brain. The drug therapy or electrical stimulation blocks activity of the CM-Pf complex of the thalamus to achieve the desired result.

Figure 1:
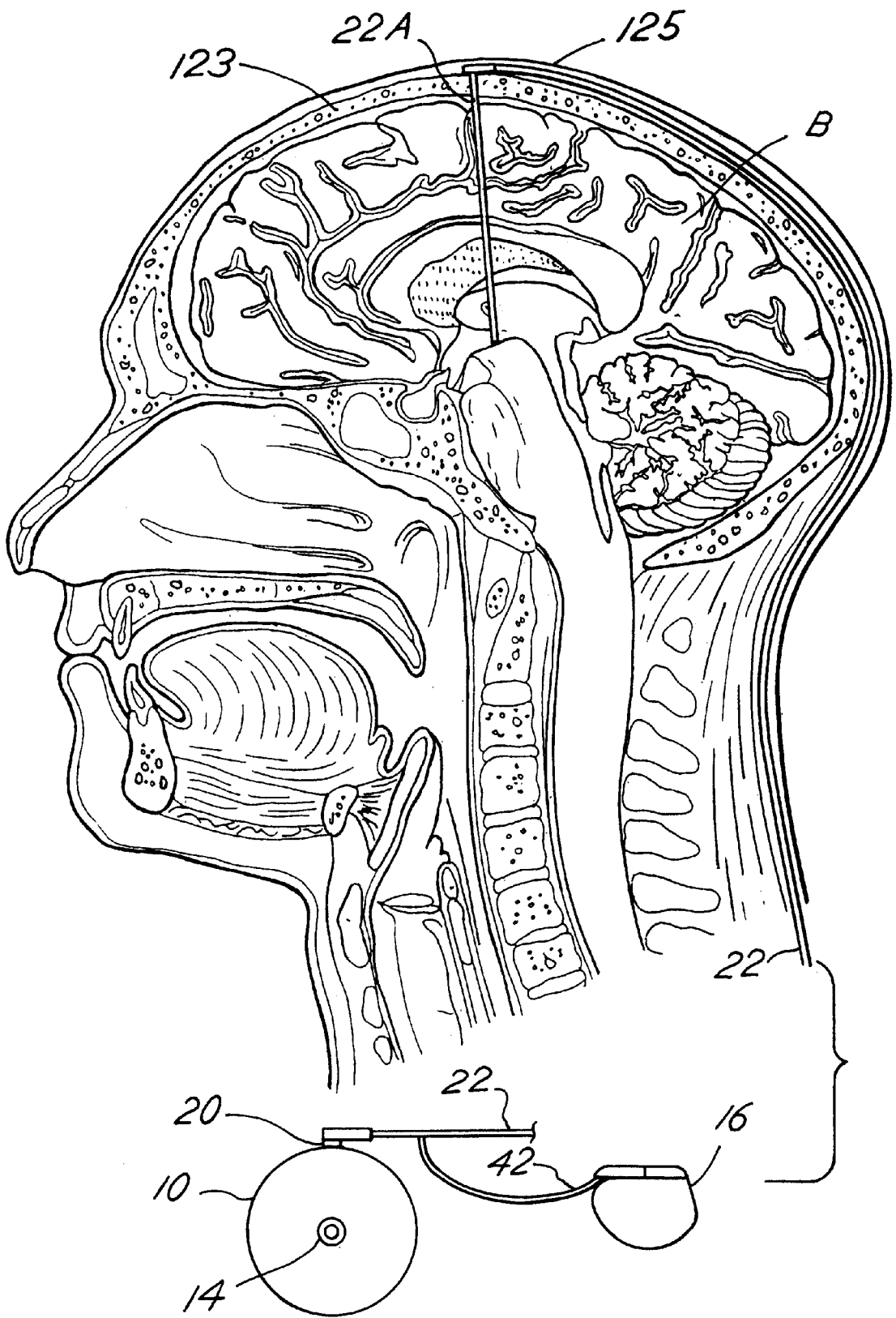
FIG. 1 is a diagrammatic illustration of a combined catheter and electrode implanted in a brain according to a preferred embodiment of the present invention, and a signal generator and pump coupled to the combined catheter and electrode.

FIG. 1 is a diagrammatic illusion of a combined catheter-electrode 22 implanted in a brain B according to a preferred embodiment of the present invention, and a signal generator 16 and a pump 10 coupled to the combined catheter-electrode 22. Pump 10 made in accordance with the preferred embodiment may be implanted below the skin of a patient. The pump 10 has a port 14 into which a hypodermic needle can be inserted through the skin to inject a quantity of a liquid agent, such as a medication or drug. The liquid agent is delivered from device 10 through a catheter port 20 into the catheter. The catheter is positioned to deliver the agent to specific infusion sites in a brain B. Pump 10 may take the form of the device shown in U.S. Pat. No. 4,692,147 (Duggan), assigned to Medtronic, Inc., Minneapolis, Minn., is incorporated by reference. An embodiment of pump 10 may be found in the Synchromed™ Infusion System manufactured by Medtronic, Inc. of Minneapolis, Minn. Those skilled in the art, however, will appreciate that pump 10 may take the form of any device used for moving fluid from a reservoir.

Signal generator 16 made in accordance with the preferred embodiment also may be implanted below the skin of a patient. Signal generator 16 may take the form of a signal generator Model 7424 manufactured by Medtronic, Inc. of Minneapolis, Minn. under the trademark Itrel II. Although any device for delivery of electrical signals may be used. Signal generator 16 is implanted in the patient's body preferably in a subcutaneous pocket located over the chest cavity or the abdomen. While shown as separate devices in FIG. 1, pump 10 and signal generator 16 could be incorporated into a common device.

As preferred, the combined electrode-catheter 22 terminates with a cylindrical hollow tube 22A having a distal end 25 implanted into a portion of the brain by conventional stereotactic surgical techniques. FIG. 3 is a diagrammatic view of tube 22A and FIG. 2 is a cross-sectional view of tube 22A taken along line 2—2 of FIG. 3. Referring to FIG. 3, a semispherical portion 23 at the distal end 25 of tube 22A provides a rounded profile for minimizing tissue disruption during insertion. End 25 is provided with microporous portions 27–29 to allow infusion and filtering of a liquid agent. Microporous portions 27–29 are preferably composed of a porous material such as polysulfone hollow fiber, manufactured by Amicon, although polyethylene, polyamides, polypropylene and expanded polytetrafluoroethylene (ePTFE) are also suitable. In a preferred embodiment, the pore size is approximately less than or equal to 0.22 microns. It is preferred that the maximum pore size be less than or equal to approximately 0.22 microns to prevent any derelict bacterial agents that may be present inside tube 22A from entering into the brain B. Furthermore, at larger pore sizes, there is the potential for tissue in-growth that may restrict the flow of agents out of the microporous portions 27–29. Alternatively, end 25 may have multiple holes or slits in which case filtering of the liquid agent may occur within pump 10. End 25 may have any number of geometries for infusion and filtering of liquid agents into the brain B.

Referring to FIG. 2, tube 22A includes an outer cylindrical insulating jacket 30 and an inner cylindrical insulating jacket 32 that defines a cylindrical catheter lumen 34. A multifilar coil of wire 36 is embedded in tube 22A as shown. Alternatively, wire 36 could consist of multifilar stranded wire.

Referring back to FIG. 3, end 25 of tube 22A terminates with one or more stimulation electrodes 38 and 40. Each electrode 38 and 40 is individually connected to signal generator 16 through a conductor in wire bundle 36 (FIG. 2). The wire bundle 36 exits the combined electrode-catheter 22 to form a cable 42 which is joined to the implanted signal generator 16 in the manner shown in FIG. 1. While the preferred embodiment shows two electrodes on tube 22A (FIG. 3), some brain locations may require a greater number. In addition, tube 22A may have only one electrode using a portion of the case of the signal generator 16 (FIG. 1) as the reference electrode. Furthermore, in some instances infusion conduit 34 (FIG. 2) and conductor conduit 36 may not be concentric tubes but rather separate conduits located beside each other in a common tube as is embodied in U.S. Pat. No. 5,458,629 (Baudino et al.), incorporated by reference. Combined electrode-catheter 22 may be coupled to a single tube 22A or tube 22A may be divided into twin tubes tube 22A and a second tube (not shown), that are implanted into the brain bilaterally. In the case of twin tubes, electrical stimulation and drug infusion may be achieved at different sites.

When selecting the tube 22A to use with a particular drug or agent, care should be taken to ensure that the particular agent will be compatible with the material from which the inner cylindrical insulating jacket 32 is composed. The inner cylindrical insulating jacket 32 and outer cylindrical insulating jacket 30 should be sufficiently flexible to facilitate insertion of the catheter 22 into brain B. The outer cylindrical insulating jacket 30 is preferably biocompatible. While it is also desirable to have the inner insulating jacket 32 be biocompatible it may not be absolutely necessary provided that the inner insulating jacket 32 can be kept from contacting the biological tissue. An enhanced tear resistant silicone elastomer or polyurethane are examples of materials that could be used. A durometer shore value of 80 is preferred.

Tube 22A is surgically implanted through a hole in the skull 123 and combined electrode-catheter 22 is implanted between the skull and the scalp 125 as shown in FIG. 1. A stylet may be placed into the center of tube 22A to give it stiffness when introducing the tube into the brain. After the stylet is removed, center lumen 34 constitutes a catheter to infuse an agent, including a drug, and an electrode for electrical stimulation. The combined electrode-catheter 22 is joined to pump 10 and signal generator 16 in the manner shown. Tube 22A may be continuous with the combined electrode-catheter 22 or there may be an intervening connection most likely at the burr hole or located somewhere along the subcutaneous path.

Figure 4:
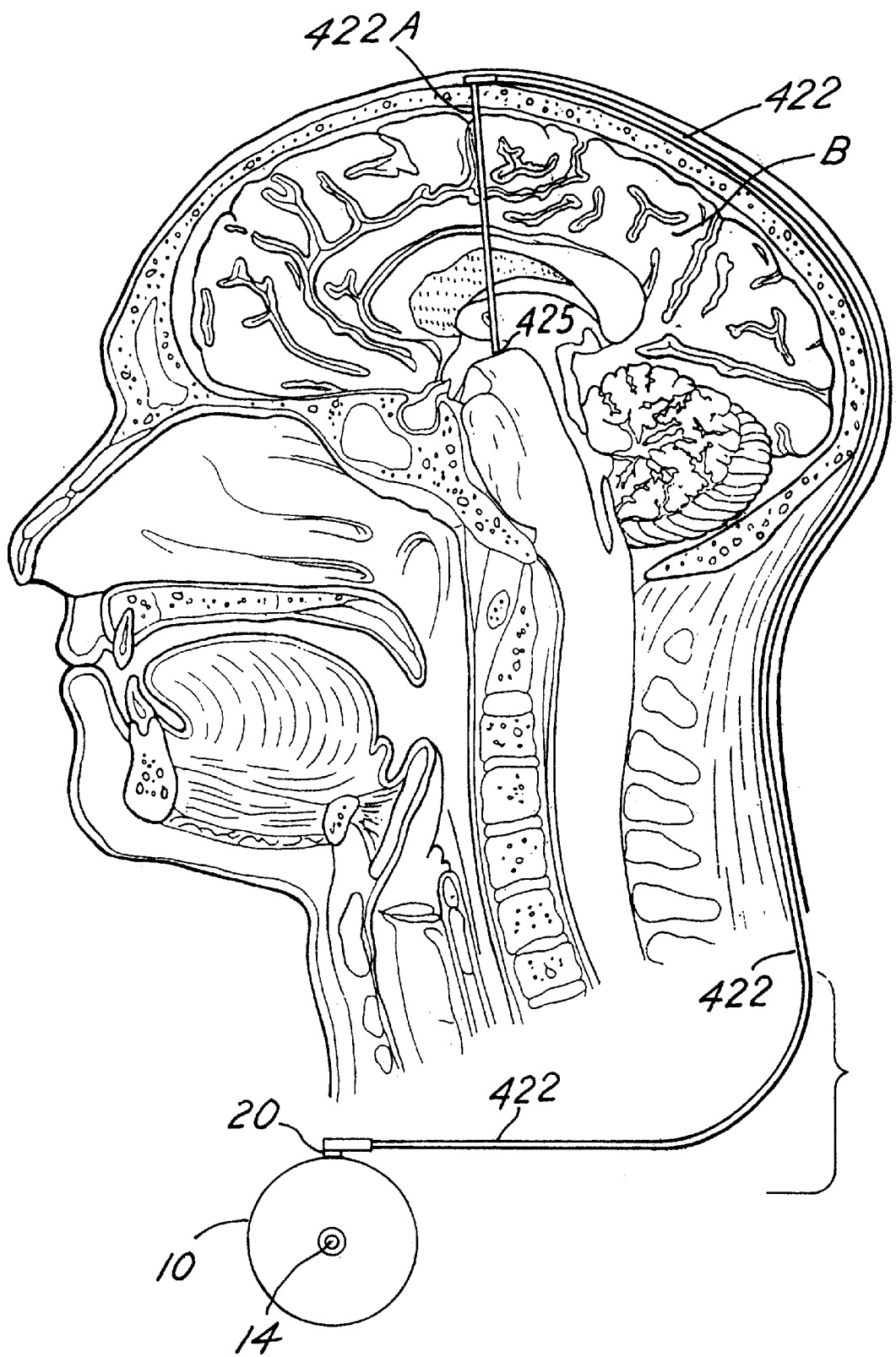
FIG. 4 is a diagrammatic illustration of a catheter implanted in a brain and a pump coupled to the catheter.

FIG. 4 discloses an another embodiment of the present invention having only a pump 10 and catheter 422. Under this embodiment, catheter 422 may take the form of a lead catheter combination developed for use outside of the dural covering of the spinal cord to treat pain An example of such a catheter is shown in U.S. Pat. No. 5,423,877 (Mackey) which is incorporated herein by reference. Alternatively, catheter 422 may be a catheter developed for use outside of the dura to treat pain in which the center lumen terminates in a single opening at the distal end 425 of tube 422A. An example of such a catheter is depicted in U.S. Pat. Nos. 5,119,832 and 5,458,631 (Xavier) which are incorporated herein by reference. Catheter 422 may be coupled to a single tube 422A or tube 422A may be divided into twin tubes, tube 422A and a second tube (not shown), that are implanted into the brain bilaterally. The second tube may be supply drugs from a second catheter and pump or may supply drugs from catheter 422 to a second location within the brain B.

Figure 5:
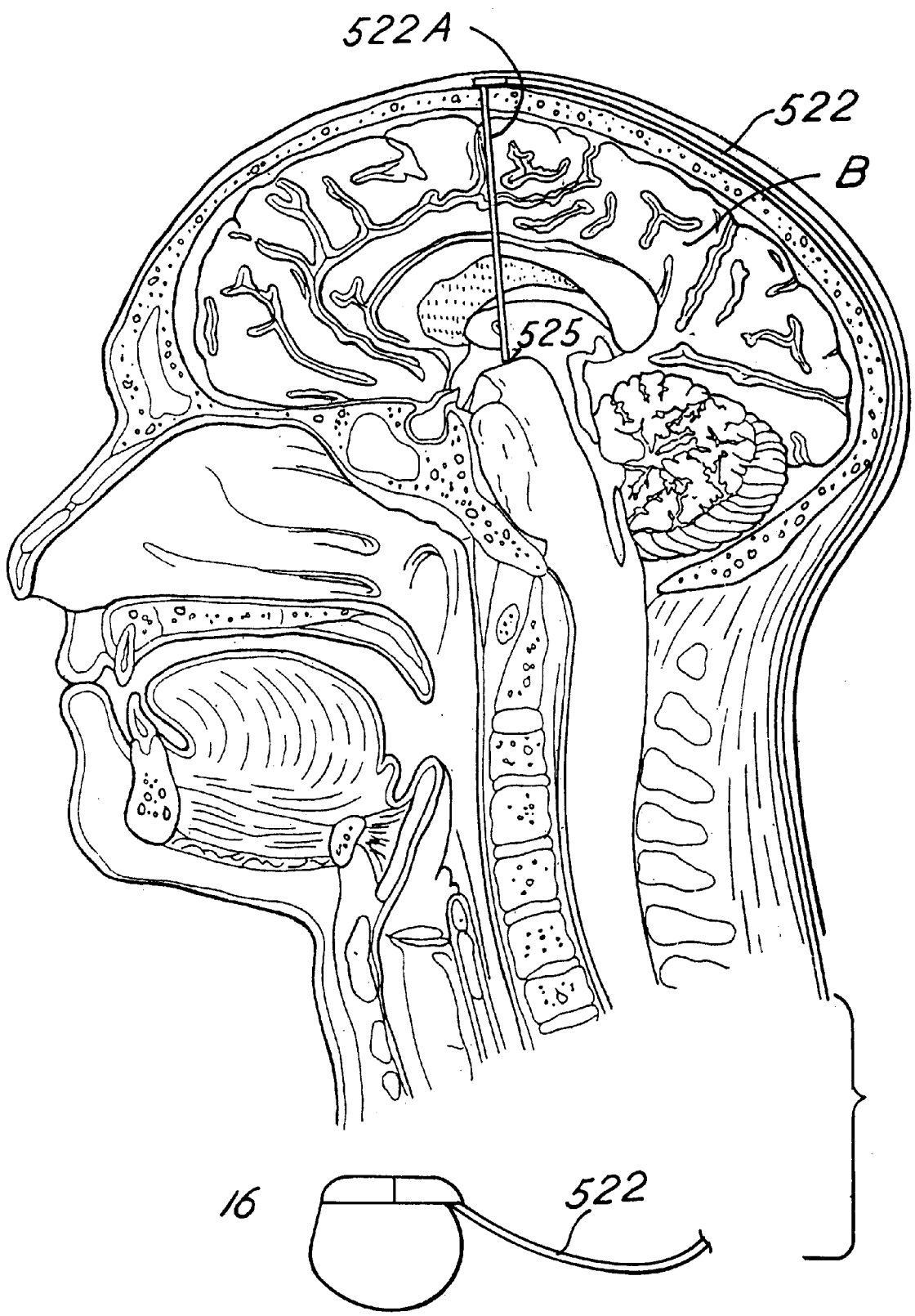
FIG. 5 is a diagrammatic illustration of a lead implanted in a brain and a signal generator coupled to the lead.

FIG. 5 discloses yet another embodiment having only a signal generator 16 and one or more stimulation electrodes at the end 525. Lead 522A may take the form of any of the leads sold with the Model 7424, for stimulating the brain, and is coupled to signal generator 16 by a conventional conductor 522. Alternatively, lead 522A may take the form of any lead for deep brain stimulation. A second lead (not shown) may alternatively be used to stimulate another portion of the brain. The second lead may be coupled to the same signal generator 16 or another signal generator. Stimulation electrodes 525 at the end of lead 522A are coupled to signal generator 16 (and possibly other signal generators) through lead 522A. Additional leads are also conceivable each having similar or differing stimulation patterns.

Figure 10:
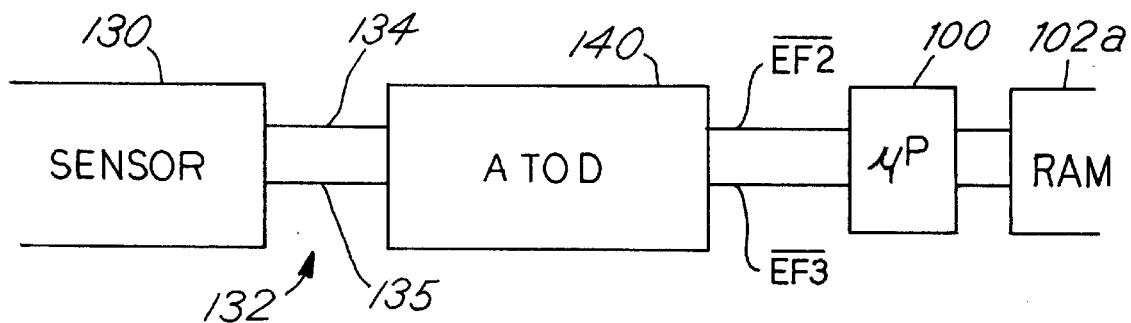
FIG. 10 is a schematic block diagram of a microprocessor and related circuitry for utilizing the sensor to control drug delivery to the brain.

With respect to drug infusion aspects of the present invention (FIGS. 1 and 4), seven different drug dosages may be provided from 0 dosage to a 1.0 ml dosage with 0.1 ml increments between choices. The time interval between dosages can preferably be selected between one and twelve hours in seven choices. This is the same type of dosage and interval described in U.S. Pat. No. 4,692,147 (Duggan), assigned to Medtronic, Inc., Minneapolis, Minn. The seven drug dosages and corresponding time increments may be loaded into RAM 102a (FIG. 10 discussed herein). The selected dosage and interval of a drug is then delivered, as described in the U.S. Pat. No. 4,692,147 through catheter 22 and tube 22A to a selected location in the brain appropriate for the treatment of the AIM disorder. One such specific site in a brain (B) is the Centremedian-Parafasicularis nucleus of the thalamus (CM-Pf complex) which has reciprocal connections to the internal pallidum (GPi). The type of drugs admit by device 10 into the brain depend on the specific location at which distal end 25 of tube 22A is surgically implanted. The appropriate brain locations to surgically implant distal end 25, the desired action on the neurons at that location and the types of drug agents useful at that location are provided in the following Table I:

TABLE I

| EFFECT | PORTION OF BRAIN | DRUG |
|---|---|---|
| DECREASE NEURAL ACTIVITY | CENTREMEDIAN-PARAFASICULARIS NUCLEUS | ANESTHETIC/GABA AGONIST |
| DECREASE EXCITATION | VL THALAMUS | GLUTAMATE ANTAGONIST/ DEGRADING ENZYME |
| INCREASE INHIBITION | VL THALAMUS | GABA AGONIST/ REUPTAKE BLOCKER |
| INCREASE EXCITATION | GPi/SNr | GLUTAMATE AGONIST/ REUPTAKE BLOCKER |
| DECREASE INHIBITION | GPi/SNr | GABA ANTAGONIST/ DEGRADING ENZYME |
| INCREASE EXCITATION | STN | GLUTAMATE AGONIST/ REUPTAKE BLOCKER |
| DECREASE INHIBITION | STN | GABA ANTAGONIST/ DEGRADING ENZYME |
| DECREASE NEURAL ACTIVITY | CENTREMEDIAN-PARAFASICULARIS NUCLEUS | ANESTHETIC/GABA AGONIST |
| DECREASE EXCITATION | VL THALAMUS | GLUTAMATE ANTAGONIST/ DEGRADING ENZYME |
| DECREASE EXCITATION | GPe | GLUTAMATE ANTAGONIST/ DEGRADING ENZYME |
| INCREASE INHIBITION | GPe | GABA AGONIST/ REUPTAKE BLOCKER |
| INCREASE EXCITATION | Neostriatum (Indirect pathway) | GLUTAMATE AGONIST/ REUPTAKE BLOCKER |
| DECREASE INHIBITION | Neostriatum (Indirect pathway) | DOPAMINE ANTAGONIST/ DEGRADING ENZYME |
| DECREASE EXCITATION | Neostriatum (Direct pathway) | GLUTAMATE ANTAGONIST/ DEGRADING ENZYME |
| DECREASE EXCITATION | Neostriatum (Direct pathway) | DOPAMINE ANTAGONIST/ DEGRADING ENZYME |
| INCREASE EXCITATION | Motor Cortex | GLUTAMATE AGONIST |

Coordinates for the portions of the brain described in Table I are as follows:

TABLE II

| BRAIN REGION | MEDIAL-LATERAL DIMENSION | DORSAL-VENTRAL DIMENSION | ANTERIOR-POSTERIOR DIMENSION |
|---|---|---|---|
| CM-Pf | 0.5 to 1.5 | 0.5 to −0.2 | −0.2 to −1.0 |
| VL Thalamus | 0.7 to 1.8 | 1.5 to −0.2 | 0.0 to −1.0 |
| GPI | 0.5 to 2.0 | 0.5 to −0.7 | 0.7 to 2.0 |
| SNr | 0.5 to 1.5 | −0.6 to −1.5 | 0.7 to −0.7 |
| STN | 0.5 to 2.0 | 0.0 to −1.0 | 0.6 to −1.0 |
| GPe | 1.6 to 2.7 | 1.0 to −1.0 | 2.0 to −1.0 |
| Striatum: | | | |
| Caudate | 0.5 to 2.0 | 1.5 to 3.0 | 1.5 to 3.0 |
| Putamen | 1.2 to 3.3 | 1.5 to −1.0 | 2.5 to −1.2 |

In the foregoing table: the medial-lateral dimensions are relative to midline of the brain; the anterior-posterior dimensions are relative to the midpoint between the anterior commissure and posterior commissure with negative indicating the posterior direction; the dorsal-ventral dimensions are relative to a line connecting the midpoints of the anterior and posterior commissures with negative being ventral to; all dimensions are in centimeters.

Alternatively, these agents might be infused into the lateral ventricle or third ventricle of the brain or just beneath the dura above the cortex or in the intrathecal space. In this instance the drug would diffuse to the appropriate site of action.

Exemplary liquid agents which provide the desired actions identified in Table I, ranges of dosages and concentrations for the liquid agents are provided in the following Table M (muM means millimicromolar):

TABLE III

| DRUG CLASS | SPECIFIC DRUG | DOSING RANGE |
|---|---|---|
| Glutamate Agonist | D-Cyclosenne | 1–10 muM |
| | L-AP4 | 1–10 muM |
| | Carboxyphenylglycine | 10–500 muM |
| | L-glutamic acid | 1–10 muM |
| | cis-Piperidie-2,3-dicarboxylic acid | 1–10 muM |
| | (+/−)-trans-ACPD | 1–10 muM |
| | L-AP4 | 1–10 muM |
| Glutamate Antagonists | MK801 (dizocilpine) | 1–20 muM |
| | ketamine Hcl | 5–50 muM |
| | AP-3 | 1–10 muM |
| | Dextromethorphan | 1–100 muM |
| | MCPD | 0.02–10 muM |
| | dextrorphan tartrate | 1–100 muM |
| | CNQX | 1–100 muM |
| GABA Agonists | baclofen | 0.1–10 muM |
| | muscinol HBr | 100–500 muM |
| GABA Antagonists | Gabazine | 1–50 muM |
| | Saclofen | 0.5–25 muM |
| | Bicuulline | 1–100 muM |
| | picrotoxin | 10–100 muM |
| Dopamine Antagonist | (+) apomorphine Hcl | 5–20 muM |
| | spiperone Hcl | 0.1–10 muM |
| | haloperidol | 10–100 muM |
| | (−) Sulphide | 0.05–1 muM |

TABLE III-continued

| DRUG CLASS | SPECIFIC DRUG | DOSING RANGE |
|---|---|---|
| Dopamine Agonist | methanesulfonate | 1–10 muM |
|  | (−) apomorphine | 10–30 muM |
|  | pergolide |  |
| Anesthetic | Lidocaine hydrochloride | 5–20 muM |

Referring back to FIG. 1, a microprocessor (not shown) within pump 10 can be programmed so that a controlled amount of drug described in Table III can be delivered to the specific brain sites described in Table I. Similarly, a microprocessor (not shown) within signal generator 16 can be programmed so that the desired stimulation can be delivered to the specific brain sites described in Table II. Electrical simulation of neural issue may be implemented by providing pulses to electrodes 38 and 40 (FIG. 3) preferably having amplitudes of 0.1 to 20 volts, pulse widths varying from 0.02 to 1.5 milliseconds, and repetition rates preferably varying from 2 to 2500 Hz. Pulses with the selected characteristics are then delivered from signal generator 16 through cable 42, combined electrode-catheter 22, tube 22A and electrodes 38 and 40 to the targeted tissue within brain B. The appropriate stimulation pulses are generated by signal generator 16 based on the programmed values established by the clinician. The type of stimulation administered by signal generator 16 to the brain B depends on the specific location at which the electrodes 38 and 40 of tube 22A are surgically implanted and the desired action on the neurons at that location. If the neuronal activity is to be blocked, signal generator 16 will be programmed with a frequency preferably in the range 50 to 2500 HZ. If the neuronal activity is to be facilitated, the stimulus frequency is chosen preferably in the range of 2 to 100 Hz. The appropriate stimulation for use in connection with the specific locations of the brain in which tube 22A terminates, together with the effect of the stimulation on that portion of the brain for an AIM disorder is provided in the following Table IV:

The embodiments of the present invention shown in FIGS. 1, 4 and 5 are open-loop systems. The microcomputer algorithm programmed by the clinician sets the stimulation parameters of signal generator 16 and/or infusion rates of infusion pump 10. This algorithm may change the parameter values over time but does so independent of any changes in symptoms the patient may be experiencing. Alternatively, the closed-loop systems show in FIGS. 6–9 which incorporate a sensor 130 to provide feedback could be used to provide enhanced results. Sensor 130 can be used with a closed loop feedback system in order to automatically determine the level of drug delivery and/or electrical stimulation necessary to alleviate the symptoms of the AIM disorder.

Figure 6:
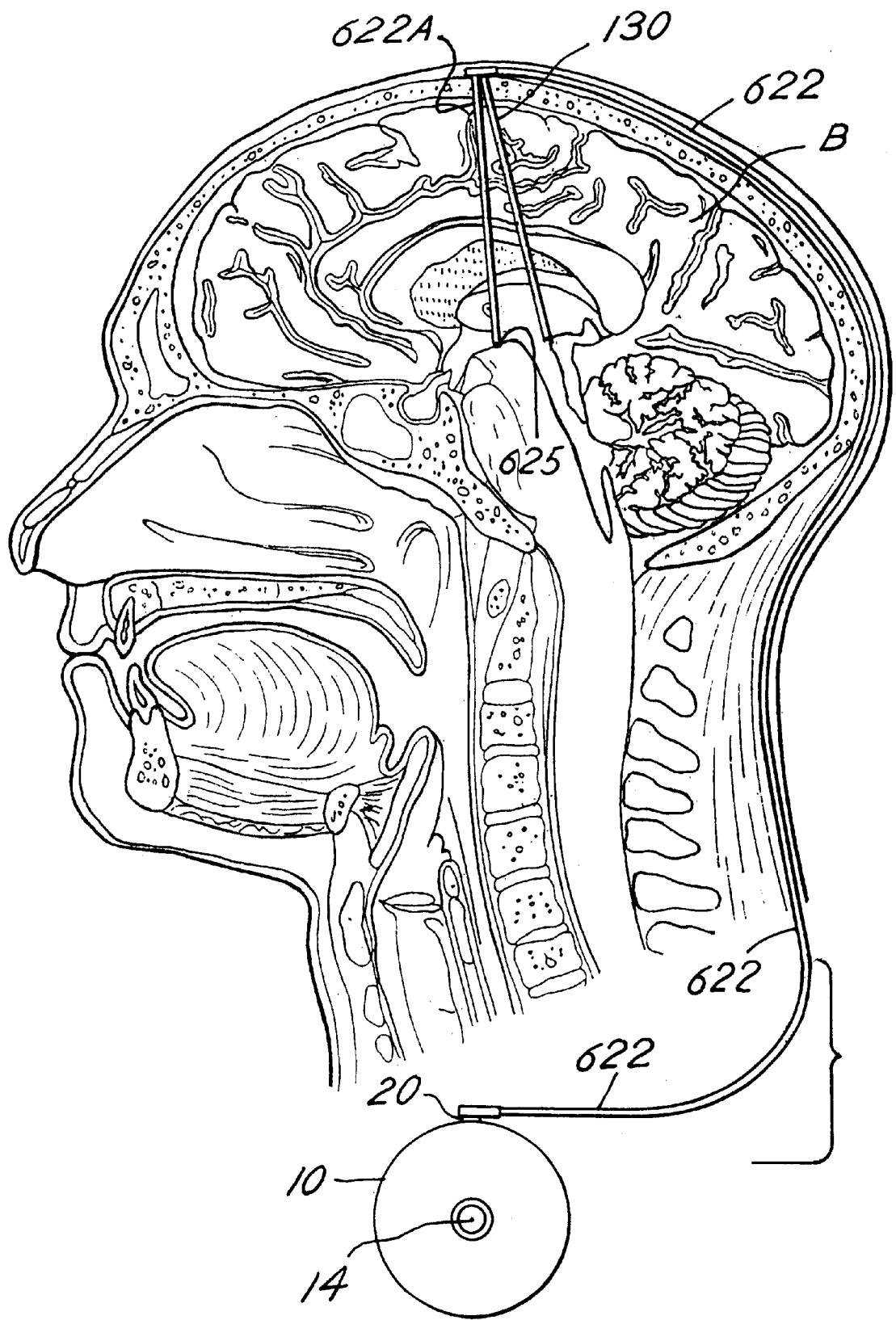
FIG. 6 is a diagrammatic illustration of a catheter and a sensor implanted in a brain and a pump coupled to the catheter and sensor.
Figure 7:
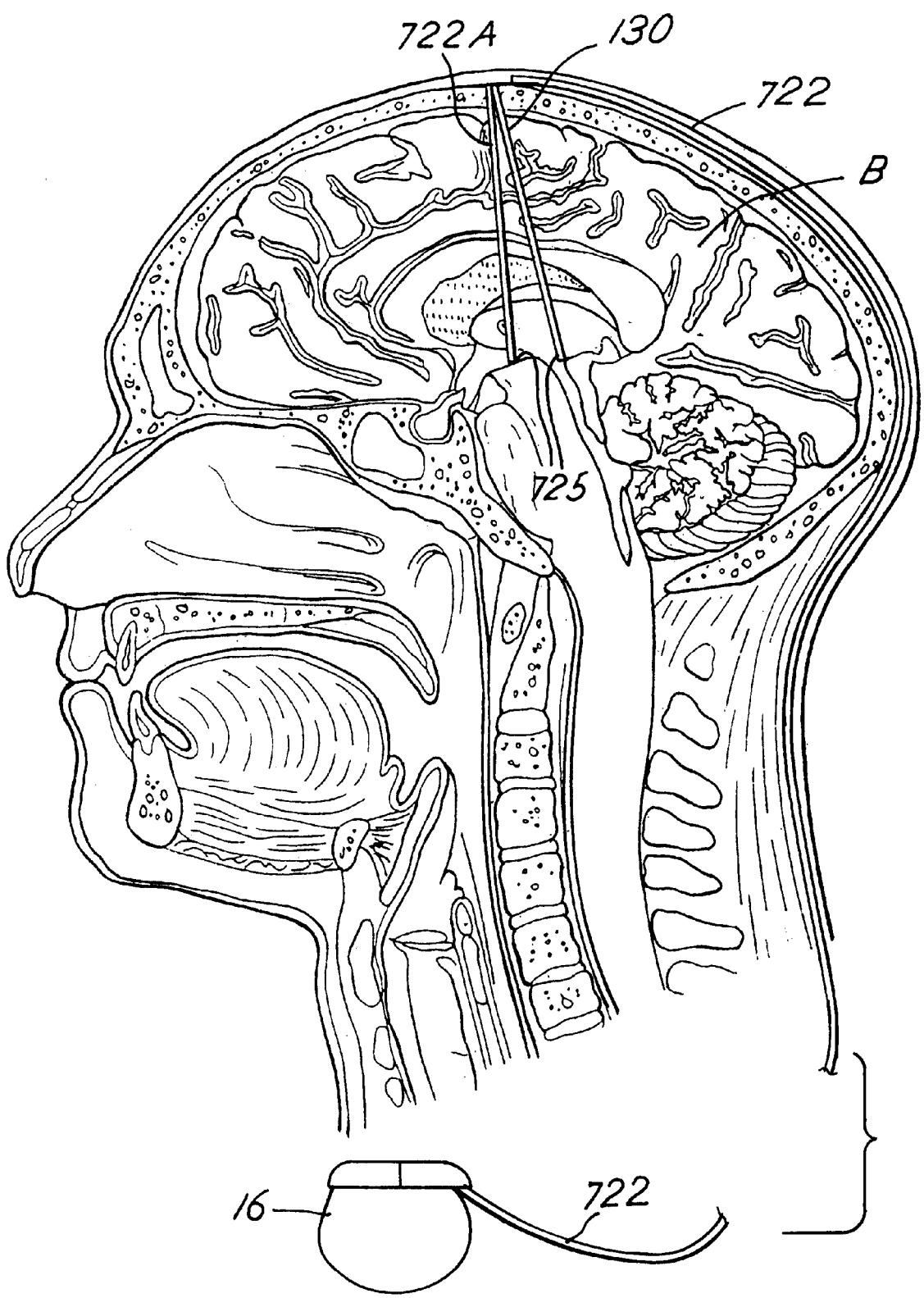
FIG. 7 is a diagrammatic illustration of a lead and a sensor implanted in a brain and a signal generator coupled to the lead and sensor.

FIG. 6 depicts an infusion pump 10 connected through tube 622 to a distal portion 622A and a separate sensor portion 130. FIG. 7 depicts a signal generator 16 connected through cable 722 which has a distal portion 722A with electrodes located at the distal end 725. Signal generator 16 is also coupled to the a separate sensor portion 130. The devices in FIGS. 6 and 7 provide "closed-loop" infusion of medication and "closed-loop" stimulation respectively.

Figure 8:
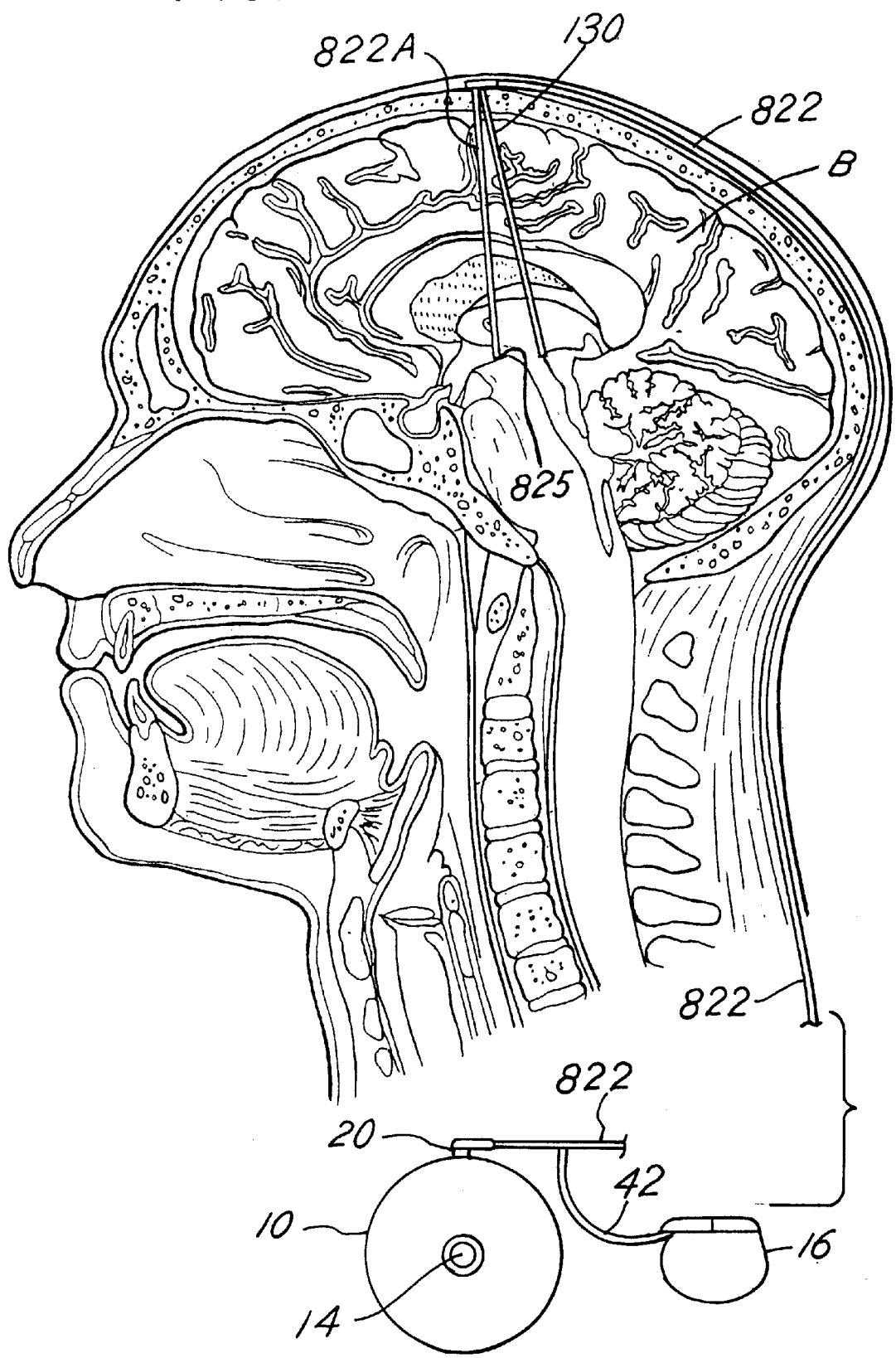
FIG. 8 is a diagrammatic illustration of a separate lead and catheter implanted in a brain and a signal generator and pump coupled to the lead and catheter respectively.
Figure 9:
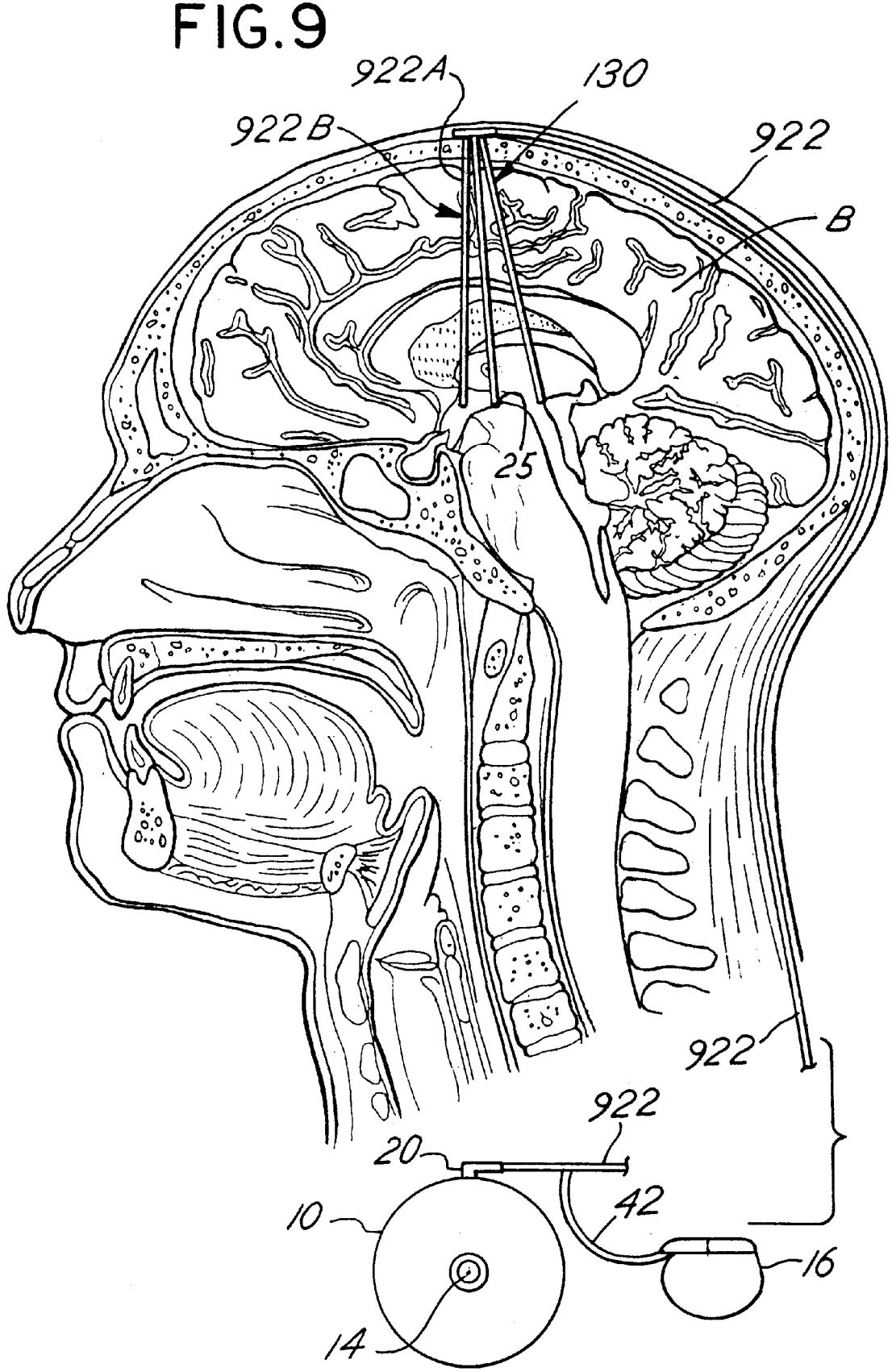
FIG. 9 is a diagrammatic illustration of a separate lead and catheter and a sensor implanted in a brain and a signal generator and pump coupled to the lead and catheter respectively and to the sensor.

Alternatively, the device in FIG. 8 combines stimulation and infusion therapies being controlled by a feedback sensor 130. In FIG. 8, the stimulation electrodes are made a part of tube 822A as depicted in FIG. 3. Alternatively, referring to FIG. 9 the stimulation electrodes could be located on a separate tube 922B away from the microporous regions located on tube 922A. This would allow delivery of stimulation to a different site in brain B than the site where medication is delivered. The sensor 130 is located at still a different site in brain B. Under certain cicumstances it may be desirable to have sensor 130 physically located on either tube 922A or tube 922B.

Sensor 130 is implanted into a portion of a patient's body suitable for detecting symptoms of the disorder being treated. Sensor 130 is adapted to sense an attribute of the symptom to be controlled or an important related symptom. For AIM disorders it is desirable to sense a physiological symptom of abnormal movement. Physiological signals

TABLE IV

| EFFECT | STIMULUS TYPE | LOCATION |
|---|---|---|
| Centremedian-parafasicularis Nucleus of Thalamus | Decrease Neuronal activity | High Frequency |
| DECREASE EXCITATION OF VL THALAMUS | HIGH FREQ. BLOCKING STIMULATION | VL THALAMUS |
| INCREASE INHIBITION OF VL THALAMUS | LOW FREQ. ACTIVATING STIMULATION | Pallido-thalamic axons (AL and LT) |
| INCREASE EXCITATION OF GPi/SNr | LOW FREQ. ACTIVATING STIMULATION | GPi/SNr |
| INCREASE EXCITATION OF GPi/SNr | LOW FREQ. ACTIVATING STIMULATION | Subthalamic to pallidal fiber tracts |
| DECREASE INHIBITION OF GPi/SNr | HIGH FREQ. BLOCKING STIMULATION | Neostriatum |
| INCREASE EXCITATION OF STN | LOW FREQ. STIMULATION | STN Nucleus |
| DECREASE INHIBITION OF STN | HIGH FREQ. BLOCKING STIMULATION | GPe |
| DECREASE EXCITATION OF GPe | HIGH FREQ. BLOCKING STIMULATION | GPe |
| INCREASE INHIBITION OF GPe | LOW FREQ. STIMULATION | Neostriatum |
| INCREASE INHIBITION OF GPe | LOW FREQ. STIMULATION | Putamen to GPe fibers (i.e., border of nucleus) |

Coordinates for the portions of the brain described in Table IV are the same as those presented in Table II.

related to muscle tension could provide feedback to adjust stimulation or infusion parameters.

For tremor, the relative motion of a joint or limb or muscle EMG may be productively sensed. Sensing electrical activity of neurons in various locations of the motor ciruitry also is helpful. Recording the electrical activity in the thalamus or cerebellum will reveal a characteristic oscillating electrical activity when tremor is present. For Ballism, Hemiballism or tremor, sensor 130 may take the form of an accelerometer detecting relative motion of a joint and limb or muscle EMG. For Dystonia sensor 130 may take the form of a device for detecting relative motion of a joint or limb or muscle EMG. For AIMs disorders that result in abnormal movement of an arm, such as arm 122, sensor 130 may be a motion detector implanted in arm 122. For example, sensor 130 may sense three dimensional or two-dimensional motion (linear rotational or joint motion), such as by an accelerometer. One such sensor suitable for use with the present invention is described in U.S. Pat. No. 5,293,879 (Vonk). Another suitable accelerometer is found in pacemakers manufactured by Medtronic, Inc. and described in patent application Ser. No. 08/399072 filed Mar. 8, 1995, in the names of James Sikorski and Larry R. Larson and entitled "Package Integrated Accelerometer". Sensor 130 also may be placed in device 10 in order to detect abnormal movement resulting from the AIMs disorder.

Sensor 130 also may be capable of detecting gravity direction or motion relative to some object (e.g., a magnet) either implanted or fixed nearby. Sensor 130 also may take the form of a device capable of detecting force in muscles or at joints, or pressure. Sensor 130 may detect muscle EMG in one, two or more muscles, or in reciprocal muscles at one joint. For such detection, sensor 130 may take the form of a lead with one or more recording electrodes inserted into the muscle of interest.

Brain EEG (e.g., cortical potentials recorded above the neurons controlling specific aspects of behavior associated with the neurological disorder) also may be detected by sensor 130. In this case, sensor 130 would take the form of an electrode with impedance values preferably chosen to optimize recording of electrical signals.

Yet another form of sensor 130 would include a device capable of detecting nerve compound action potentials (e.g., either sensory afferent information from muscle or skin receptors or efferent motor potentials controlling a muscle of interest).

Sensor 130 also may take the form of a device capable of detecting nerve cell or axon activity that is related to the pathways at the cause of the symptom, or that reflects sensations which are elicited by the symptom. Such a sensor may be located deep in the brain. For such detecting, sensor 130 may take the form of an electrode inserted into the internal capsule, motor cortex or basal ganglia of the brain. Signals of any kind that are received by the sensor may by amplified before transmission to circuitry contained within device 10 or device 16.

Sensor 130 may take the form of a transducer consisting of an electrode with an ion selective coating applied which is capable of directly reducing the amount of a particular transmitter substance or its breakdown by-products found in the interstitial space of a region of the brain such as the ventral lateral thalamus. The level of the interstitial transmitter substance is an indicator of the relative activity of the brain region. An example of this type of transducer is described in the paper "Multichannel semiconductor-based electrodes for in vivo electrochemical and electrophysiological studies in rat CNS" by Craig G. van Horne, Spencer Bement, Barry J. Hoffer, and Greg A. Gerhardt, published in *Neuroscience Letters,* 120 (1990) 249–252.

Sensor 130 may be external to the body communicating with the implanted portions through telemetry.

Referring to FIG. 10, the output of sensor 130 is coupled by a cable 132 comprising conductors 134 and 135 to the input of analog to digital converter 140. Alternatively the output of the sensor 130 could communicate through a "body bus" communication system as described in U.S. Pat. No. 5,113,859 (Funke), assigned to Medtronic which is incorporated by reference. Alternatively, the output of an external feedback sensor 130 would communicate with the implanted pulse generator 16 or pump 10 through a telemetry down-link. The output of the analog to digital converter 140 is connected to terminals EF2 BAR and EF3 BAR. Such a configuration may be one similar to that shown in U.S. Pat. No. 4,692,147 ("'147 Patent") except that before converter 140 is connected to the terminals, the demodulator of the '147 patent (identified by 101) would be disconnected. A drug can be delivered essentially continuously (within the constraints of the particular delivery device being used) or it may be delivered during intermittent intervals coordinated to reflect the half-life of the particular agent being infused or with circadian rhythms. As an example, the symptoms of the neurological disorder may normally subside at night when the person is sleeping so the drug delivery rates might be reduced to coincide with the hours between 10 p.m. and 7 a.m.

One exemplary computer algorithm is shown in FIG. 4. Microprocessor 100 included within pump 10 reads converter 140 instep 150, and stores one or more values in RAM 102*a* in step 152. One of seven dosages is selected in step 154, and an appropriate time interval is selected in step 156. The selected dosage and interval of a drug is then delivered through catheter 22 and tube 22A to the basal ganglia of the brain as described in the '147 Patent.

For some types of sensors, a microprocessor and analog to digital converter will not be necessary. The output from sensor 130 can be filtered by an appropriate elect filter in order to provide a control signal for signal generator 16. An example of such a filter is found in U.S. Pat. No. 5,259,387 "Muscle Artifact Filter, Issued to Victor de Pinto on Nov. 9, 1993, incorporated herein by reference.

Figure 12:
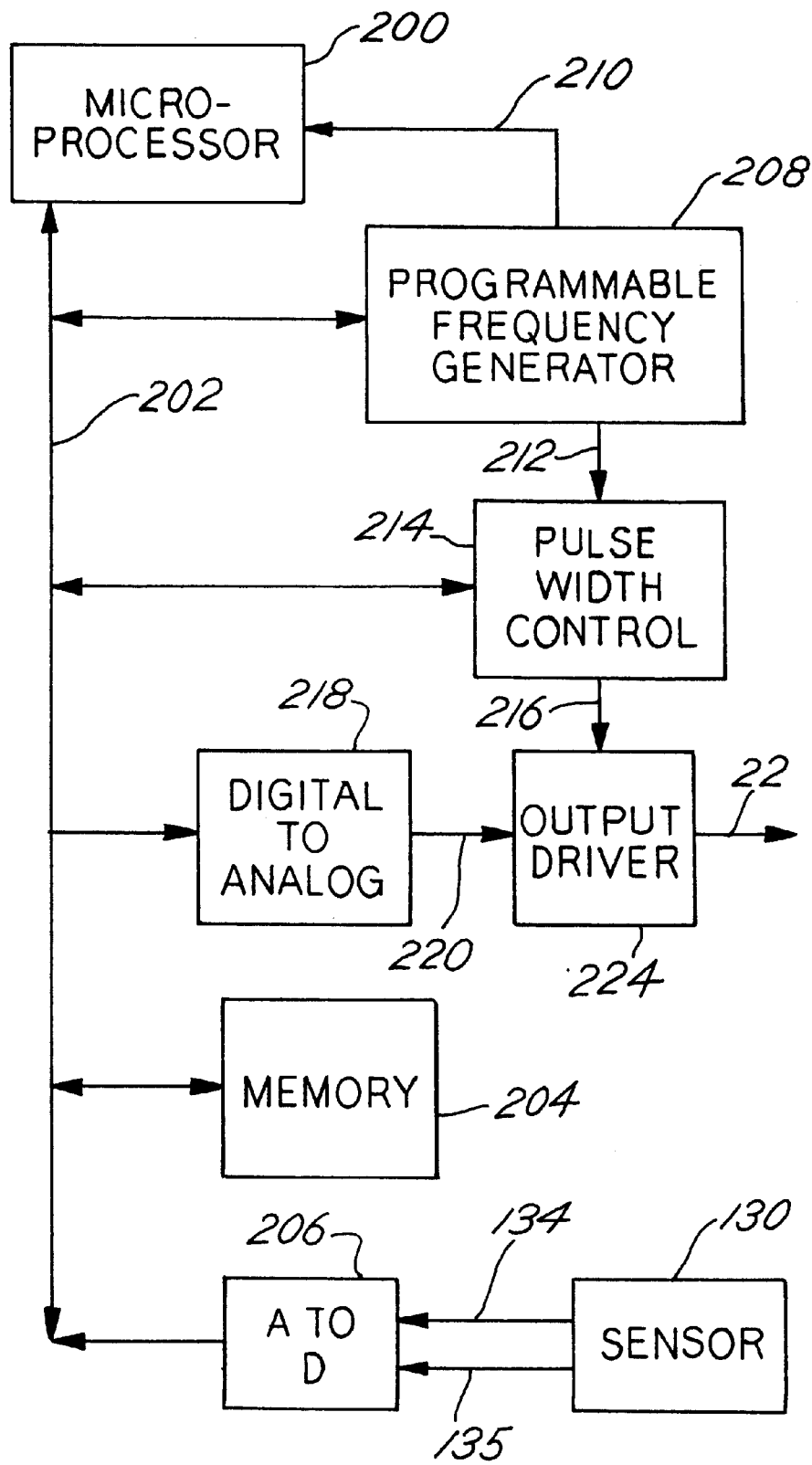
FIG. 12 is a schematic block diagram of a microprocessor and related circuitry for utilizing the sensor to control electrical stimulation administered to the brain.

Closed-loop electrical stimulation can be achieved by a modified form of the ITREL II signal generator which is described in FIG. 12. The output of the analog to digital converter 206 is connected to a microprocessor 200 through a peripheral bus 202 including address, data and control lines. Microprocessor 200 processes the sensor data in different ways depending on the type of transducer in use. When the signal on sensor 130 exceeds a level programmed by the clinician and stored in a memory 204, increasing amounts of stimulation will be applied through an output driver 224.

The stimulus pulse frequency is controlled by programming a value to a programmable frequency generator 208 using bus 202. The programmable frequency generator provides an interrupt signal to microprocessor 200 through an interrupt line 210 when each stimulus pulse is to be generated. The frequency generator may be implemented by model CDP1878 sold by Harris Corporation. The amplitude for each stimulus pulse is programmed to a digital to analog converter 218 using bus 202. The analog output is conveyed through a conductor 220 to an output driver circuit 224 to control stimulus amplitude. Microprocessor 200 also programs a pulse width control module 214 using bus 202. The pulse width control provides an enabling pulse of duration equal to the pulse width via a conductor. Pulses with the selected characteristics are then delivered from signal generator 16 through cable 22 and lead 22A or 22B to the target locations of a brain B.

Figure 11:
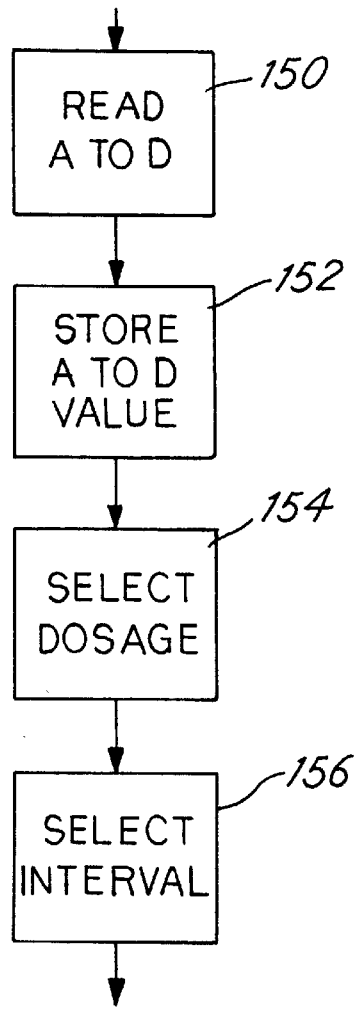
FIG. 11 is a flow chart illustrating a preferred form of a microprocessor program for utilizing the sensor to control drug dosage administered to the brain.

Microprocessor 200 executes an algorithm shown in FIGS. 13–17 in order to provide stimulation with closed loop feedback control. At the time the stimulation signal generator 16 or alternative device in which the stimulation and infusion functions are combined is implanted, the clinician programs certain key parameters into the memory of the implanted device via telemetry. These parameters may be updated subsequently as needed. Step 400 in FIG. 11 indicates the process of first choosing whether the neural activity at the stimulation site is to be blocked or facilitated (step 400(1)) and whether the sensor location is one for which an increase in the neural activity at that location is equivalent to an increase in neural activity at the stimulation target or vice versa (step 400(2)). Next the clinician must program the range of release for pulse width (step 400(3)), amplitude (step 400(4)) and frequency (step 400(5)) which signal generator 16 may use to optimize the therapy. The clinician may also choose the order in which the parameter changes are made (step 400(6)). Alternatively, the clinician may elect to use default values.

Figure 13:
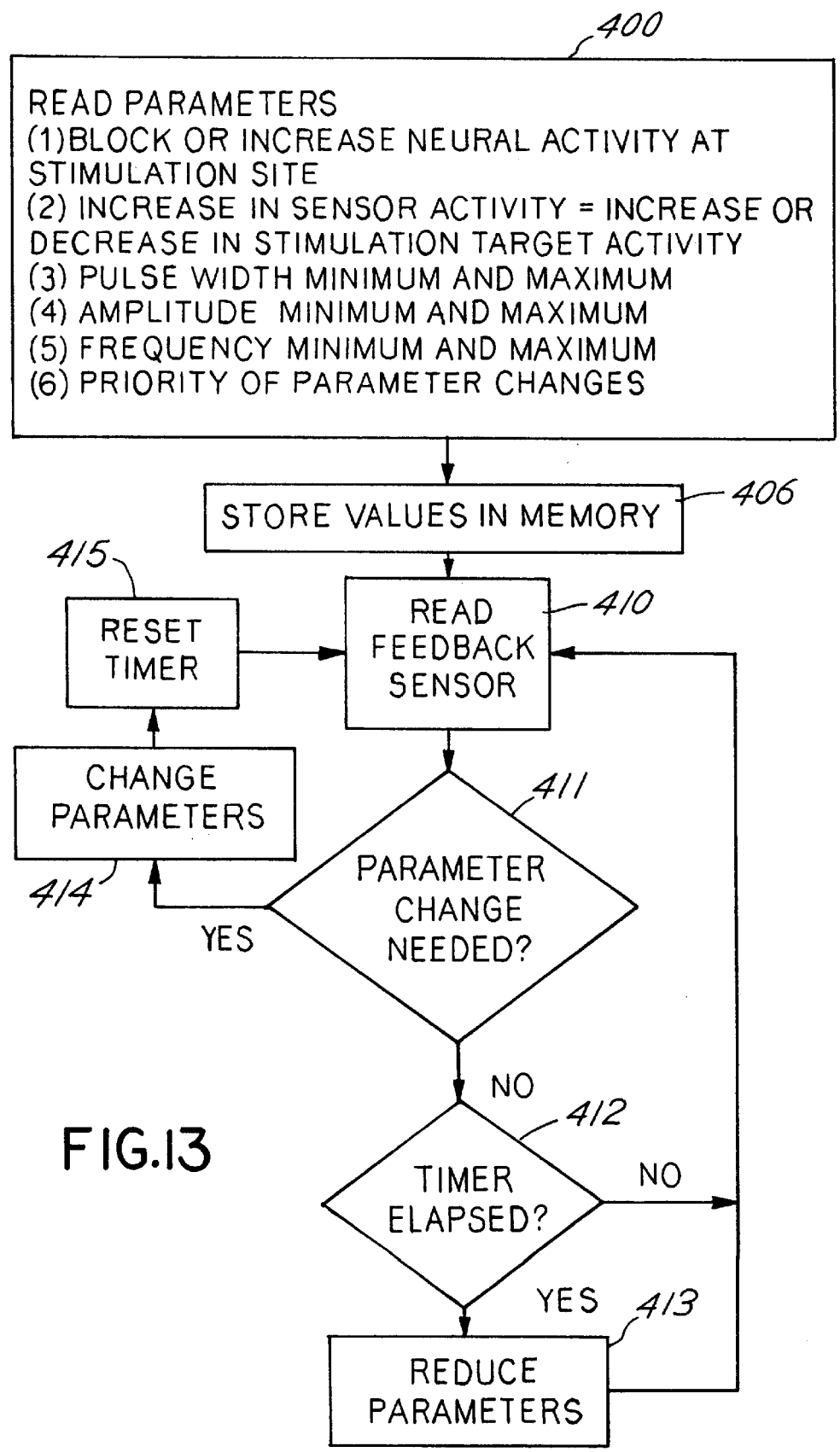
FIGS. 13–17 are flow charts illustrating a preferred form of a microprocessor program for generating electrical stimulation pulses to be administered to the brain.

The algorithm for selecting parameters is different depending on whether the clinician has chosen to block the neural activity at the stimulation target or facilitate the neural activity. FIG. 13 details steps of the algorithm to make parameter changes.

Figure 14:
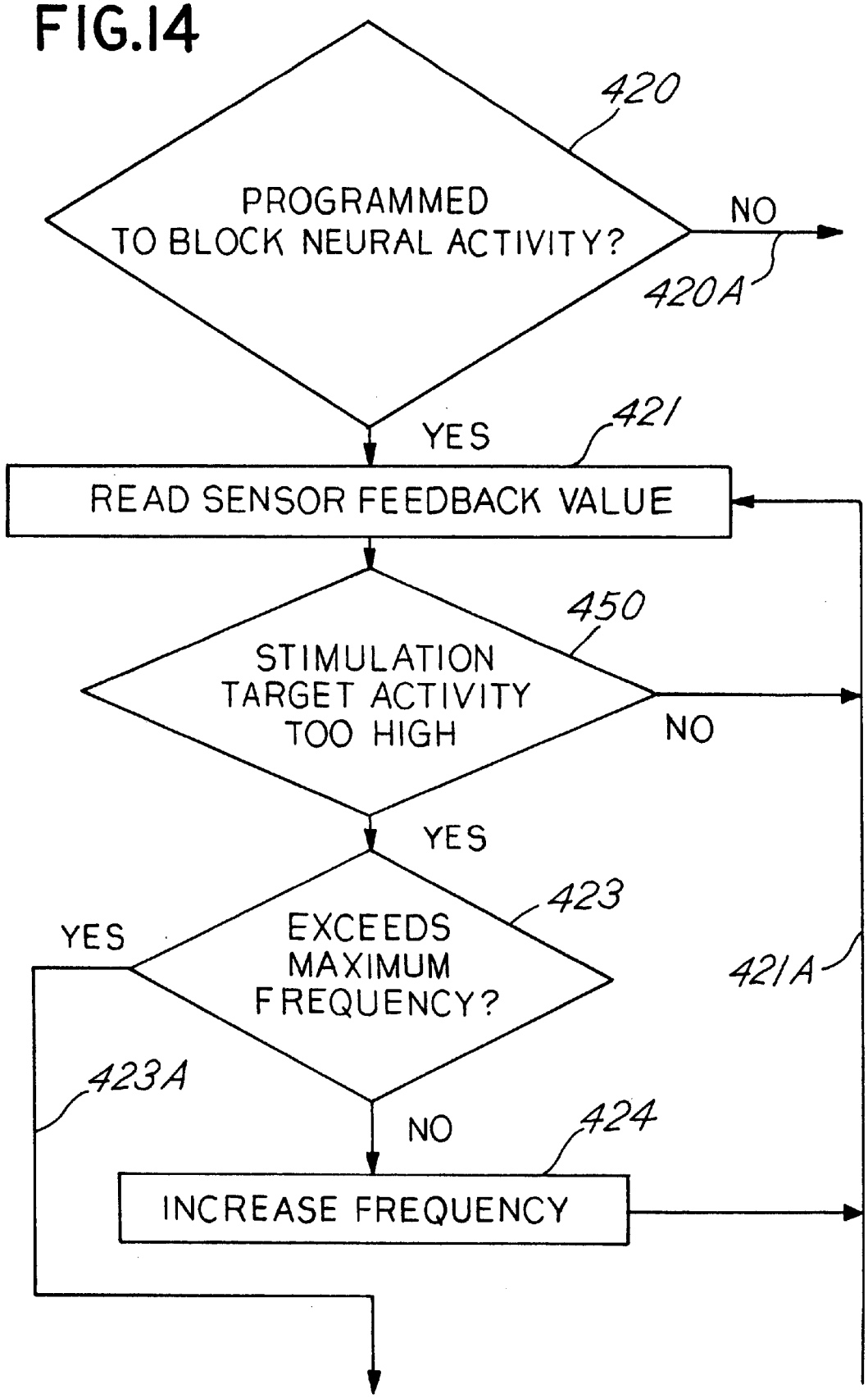
Figure 15:
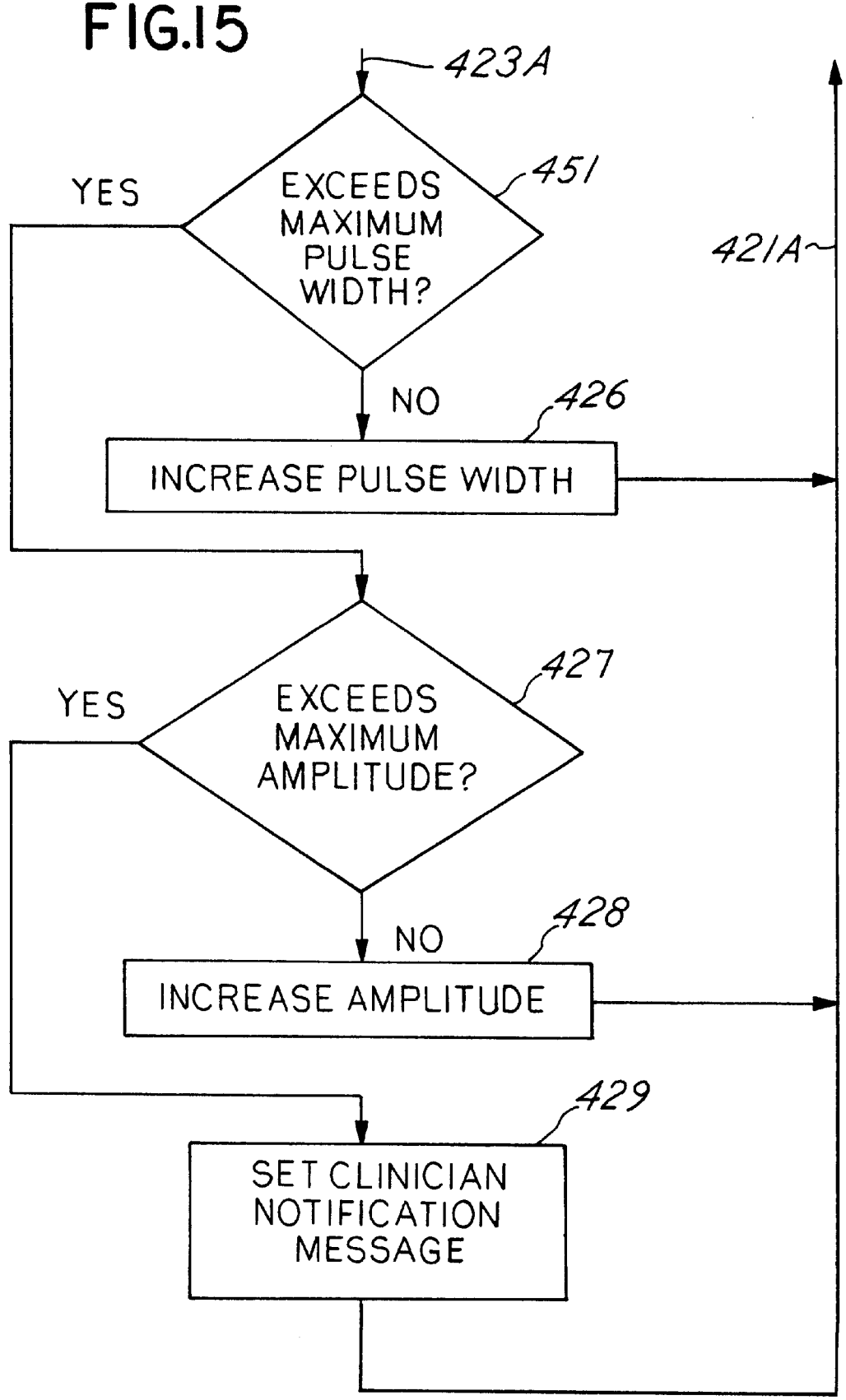
Figure 16:
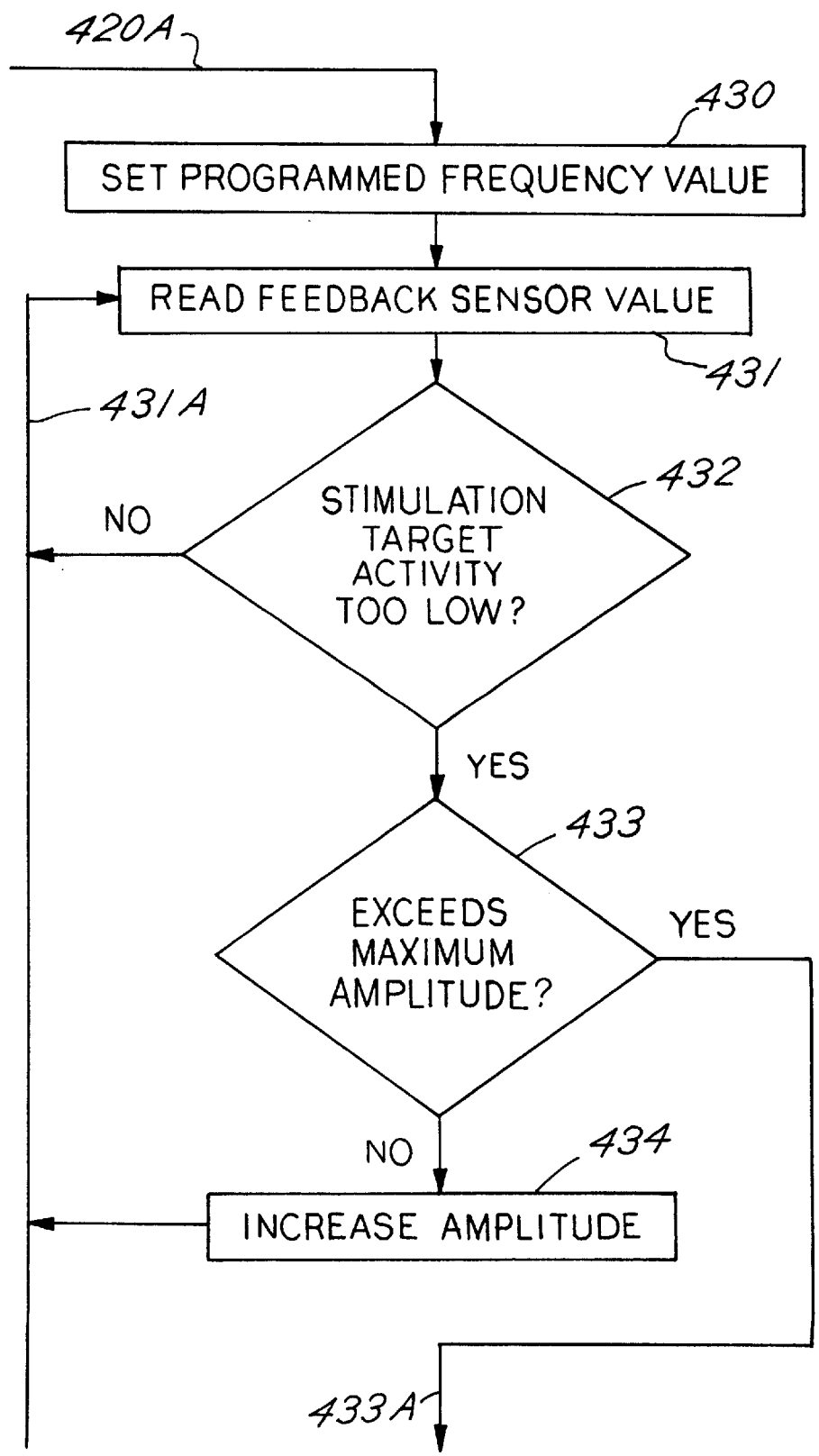

The algorithm uses the clinician programmed indication of whether the neurons at the particular location of the stimulating electrode are to be facilitated or blocked in order to decide which path of the parameter selection algorithm to follow (step 420, FIG. 14). If the neuronal activity is to be blocked, signal generator 16 first reads the feedback sensor 130 in step 421. If the sensor values indicate the activity in the neurons is too high (step 450), the algorithm in this embodiment first increases the frequency of stimulation in step 424 provided this increase does not exceed the preset maximum value set by the physician. Step 423 checks for this condition. If the frequency parameter is not at the maximum, the algorithm returns to step 421 through path 421A to monitor the feed back signal from sensor 130.

If the frequency parameter is at the maximum, the algorithm next increases the pulse width in step 426 (FIG. 15), again with the Diction that this parameter has not exceeded the maximum value as checked for in step 451 through path 423A. Not having reached maximum pulse width, the algorithm returns to step 421 to monitor the feedback signal from sensor 130. Should the maximum pulse width have been reached, the algorithm next increases amplitude in a like manner as shown in steps 427 and 428. In the event that all parameters reach the maximum, a notification message is set in step 429 to be sent by telemetry to the clinician indicating that device 16 is unable to reduce neural activity to the desired level.

Figure 17:
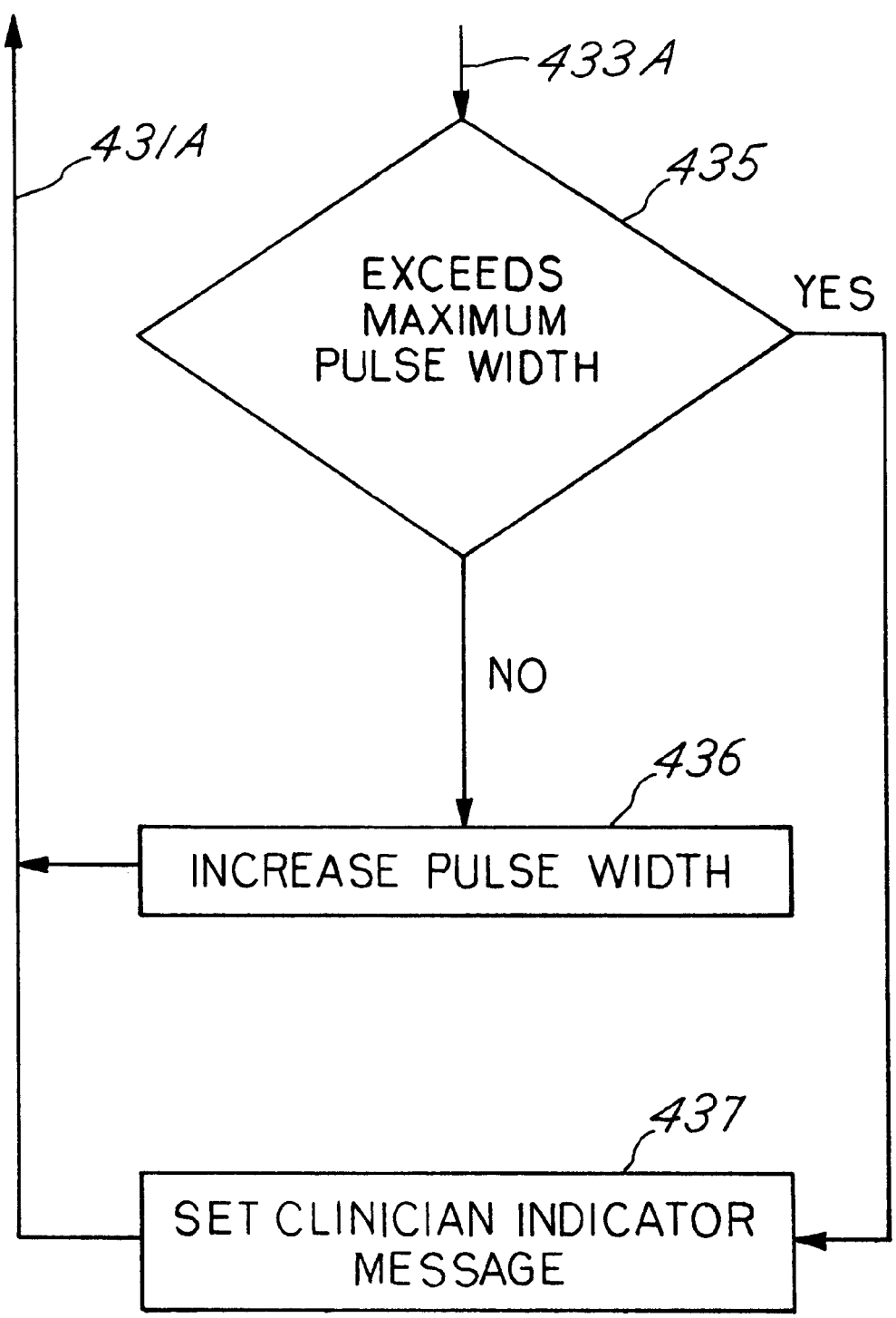

If, on the other hand, the stimulation electrode is placed in a location which the clinician would like to activate in order to alter the symptoms of the neurological disorder, the algorithm would follow a different sequence of events. In the preferred embodiment, the frequency parameter would be fixed at a value chosen by the clinician to facilitate neuronal activity in step 430 (FIG. 16) through path 420A. In steps 431 and 432 the algorithm uses the values of the feedback sensor to determine if neuronal activity is being adequately controlled. In this case, inadequate control indicates that the neuronal activity of the stimulation target is too low. Neuronal activity is increased by first increasing stimulation amplitude (step 434) provided it doesn't exceed the programmed maximum value checked for in step 433. When maximum amplitude is reached, the algorithm inccreases pulse width to its maximum value in steps 435 and 436 (FIG. 17). A lack of adequate alteration of the symptoms of the neurological disorder, even though maximum parameters are used, is indicated to the clinicianin step 437. After steps 434, 436 and 437, the algorithm returns to step 431 through path 431A, and the feedback sensor again is read.

It is desirable to reduce parameter values to the minimum level needed to establish the appropriate level of neuronal activity in, for example, the target brain nucleus. Superimposed on the algorithm just described is an additional algorithm to readjust all the parameter levels downward as far as possible. In FIG. 13, steps 410 through 415 constitute the method to do this. When parameters are changed, a time is reset in step 415. If there is no need to change any stimulus parameters before the timer has counted out, then it may be possible due to changes in neuronal activity to reduce the parameter values and still maintain appropriate levels of neuronal activity in the target neurons. At the end of the programmed time interval, signal generator 16 tries reducing a parameter in step 413 to determine if control is maintained. If it is, the various parameter values will be ratcheted down until such time as the sensor values again indicate a need to increase them. While the algorithms in FIGS. 13–17 follow the order of parameter selection indicated, other sequences may be programmed by the clinician.

Figure 18:
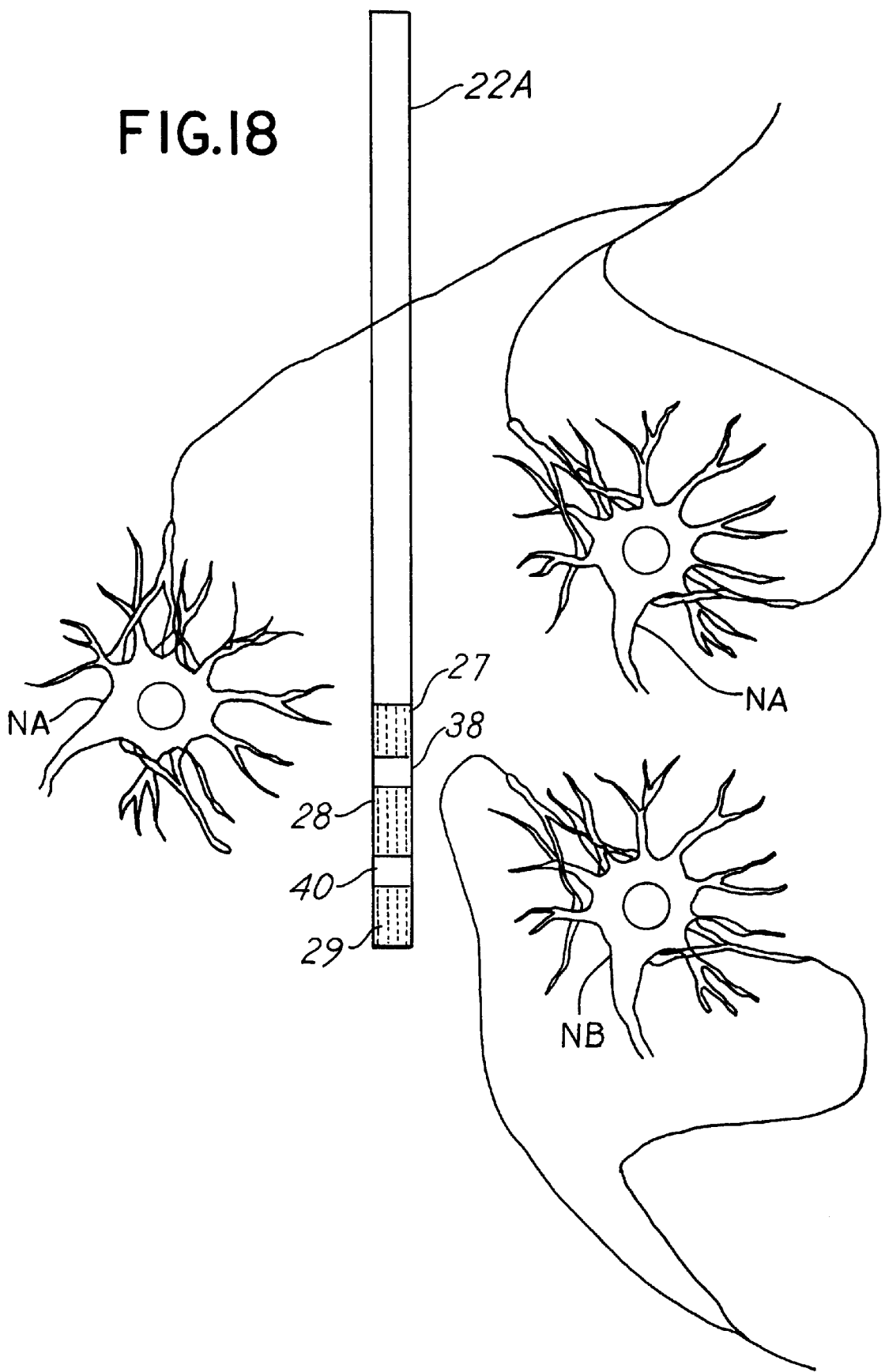

The foregoing techniques for simultaneous drug infusion and electrical stimulation can be applied to neural tissue in general, and are not limited to the previously described locations in the brain. FIG. 18 describes one such application in which type A neurons, such as NA, are located in the same region as type B neurons, such as NB which can typically be found in a brain. By infusing various agents through portions 27–29, neurons NA can be inhibited or excited with respect to their response to electrical stimulation provided by electrodes 38 and 40, while neurons NB remain unchanged with respect to their response to such stimulation. Thus, neurons NA or NB can be selectively stimulated by electrodes 38 and 40 due to the infusion of substances through portions 27–29 of tube 22A.

Referring to FIG. 19, a neuron N1 found in a brain has a cell body CB1 and a nucleus NU1. Neuron N1 can be excited by axon terminals AT1 at synapses SN1–SN2 by an inhibitory neurotransmitter TRB and can be excited by axon terminals AT2 at synapses SN4–SN6 by an excitatory neurotransmitter TRA. Portions 27–29 are used to infuse into the region of neuron N1 one or more of the following agents: an antagonist of transmitter TRB, an agonist of transmitter TRA, an agent to block the reputake of transmitter TRA, a degradative enzyme for transmitter TRB and potassium The agents can be infused stately or together in a cocktail. Such infusion leads to partial depolarization of neuron N1 and to a reduced threshold to stimulation by electrodes 38 and 40. That is, after infusion, the amplitude of stimulation required to create action potentials in neuron N1 is reduced compared to the time period before infusion.

Figure 20:
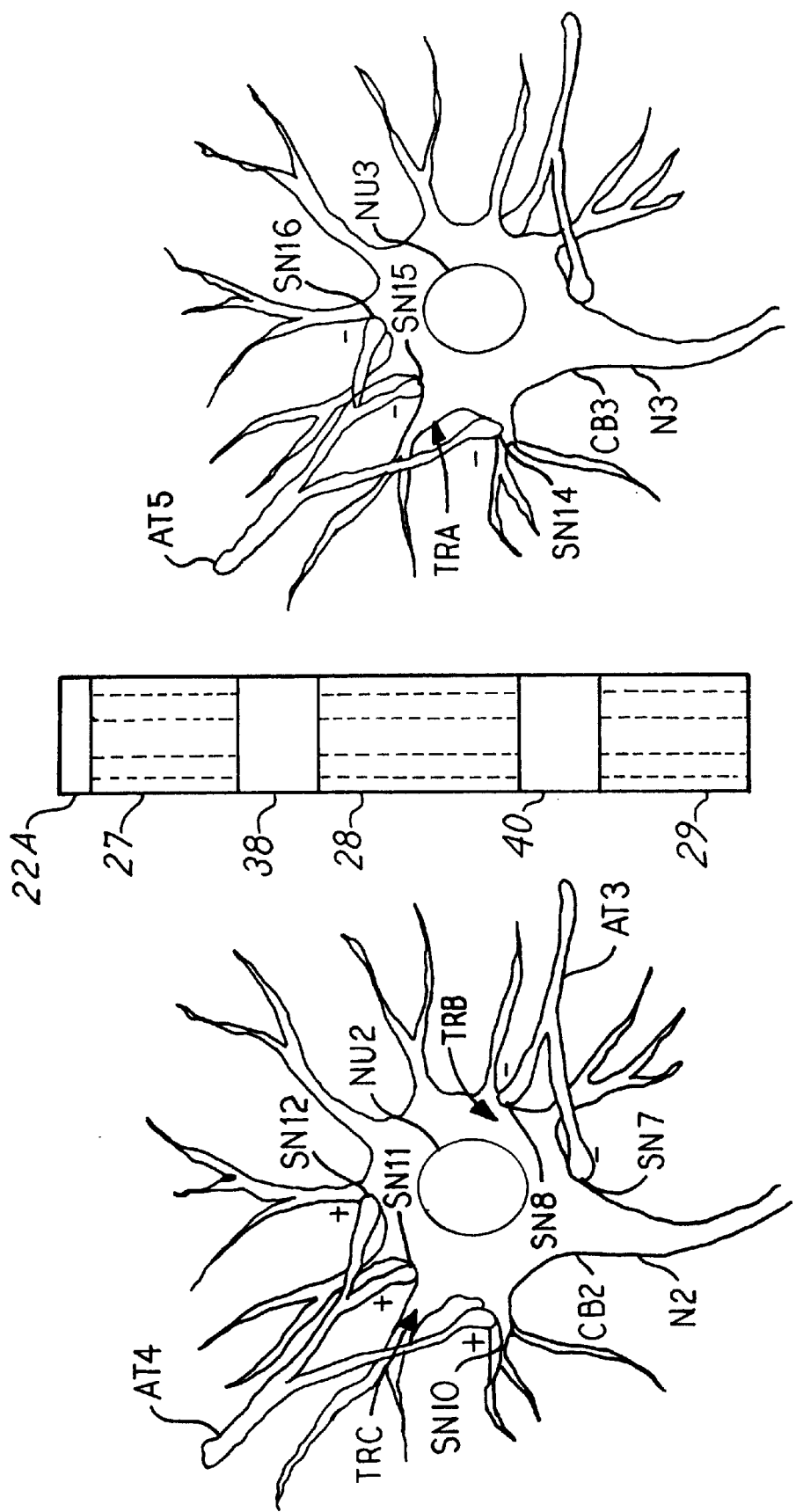

Referring to FIG. 20, a neuron N2 found in a brain has a cell body CB2 and a nucleus NU2. Neuron N2 can be inhibited by axon terminals AT3 at synapses SN7–SN8 by an inhibitory neurotransmitter TRB and can be excited by axon terminals AT4 at synapses SN10–SN12 by an excitatory neurotransmitter RC. A neuron N3 found in a brain has a cell body CB3 and a nucleus NU3. Neuron N3 can be inhibited by axon terminals AT5 at synapses SN14–SN16 by an inhibitory neurotransmitter TRA. Portions 27–29 of tube 22A are used to infuse into the region of neurons N2 and N3 one or more of the following agents: an agonist of transmitter TRA, an agent to block the reuptake of transmitter TRA or an agent to block a degradative enzyme for transmitter TRA. Each of these agents hyperpolarize neuron N3 and increase the potential threshold required to create action potentials in neuron N3. Therefore, neuron N2 can be selectively activated by electrodes 38 and 40 so that an action potential is created in neuron N2 without creating an action potential in neuron N3.

Selective activation of neuron N2 also can be achieved by infusing into the region of neurons N2 and N3 one or more of the following agents: an agonist for transmitter TRC, an agent to block the reuptake of transmitter IRC, an agent to block the degrading enzyme for transmitter TRC, an antagonist for transmitter TRB, an agent to enhance the reuptake of tatter TRB or a degrading enzyme for transmitter TRB. The agents can be infused separately or together in a cocktail. Such infusion leads to partial depolarization of neuron N2 and to a reduced threshold to stimulation by elecctrodes 38 and 40. That is, after infusion, the amplitude of stimulation required to create action potentials in neuron N2 is reduced compared to the time period before infusion, making it easier to electrically stimulate neuron N2 relative to neuron N3.

Figure 21:
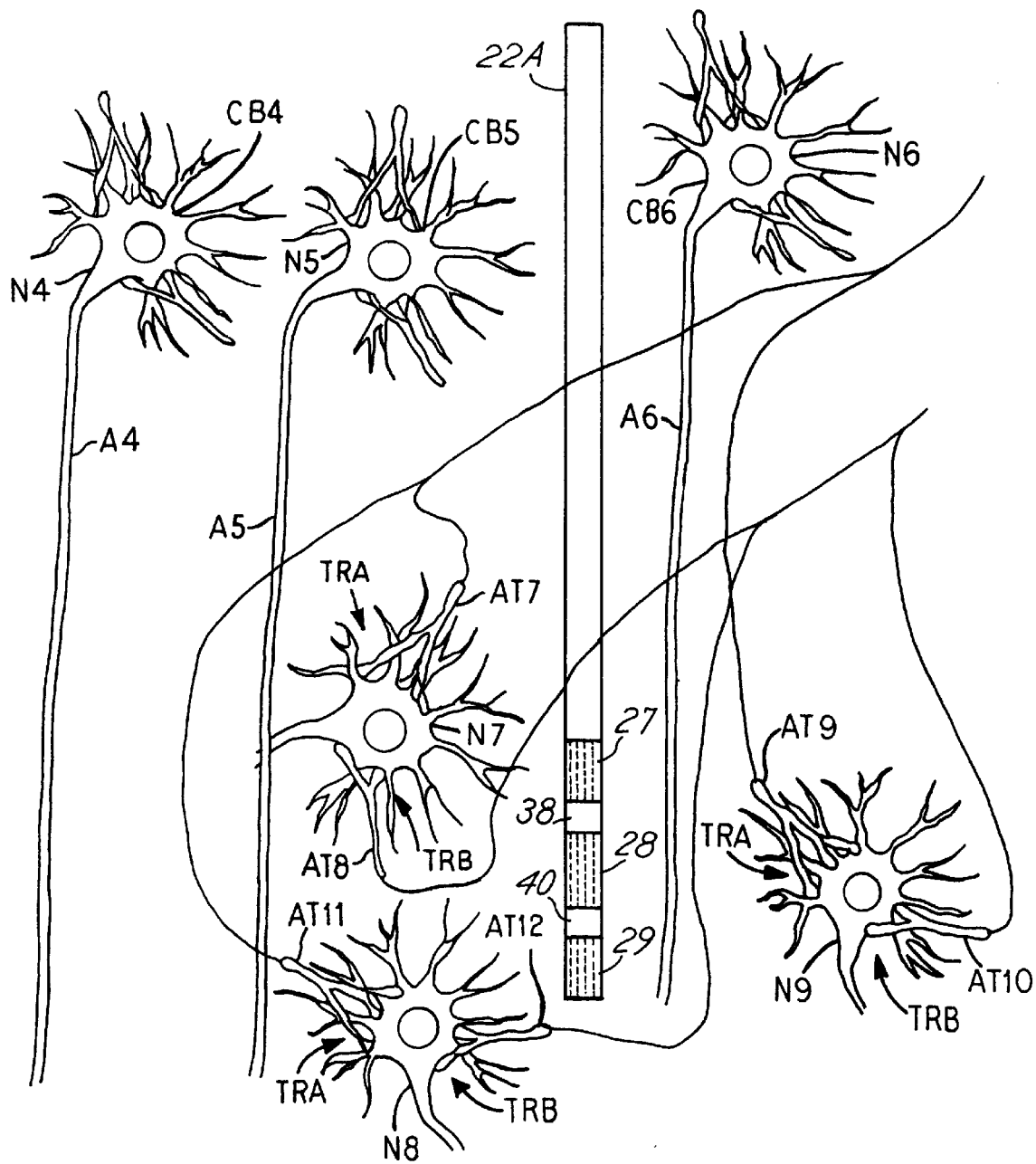

Referring to FIG. 21, neurons N4–N6 found in a brain have cells bodies CB4–CB6, respectively, and axons A4–A6, respectively, which are long fibers of passage that typically pass through white tissue in the spinal cord or brain. Cell bodies CB4–CB6 are located at portions of the body somewhat remote from infusion portions 27–29 and electrodes 38 and 40. However, portions of axons A4–A6 pass in the region of infusion portions 27–29 and electrodes 38 and 40. Neurons N7–N9 have cell bodies that are located in the region of infusion portions 27–29 and electrodes 38 and 40. Neuron N7 can be inhibited at axon terminals AT7 by an inhibitory neurotransmitter TRA and excited at axon terminals AT8 by an excitatory neurotransmitter TRB; neuron N9 can be inhibited at axon terminals AT9 by inhibitory neurotransmitter TRA and excited at axon terminals AT10 by excitatory neurotransmitter TRB; and neuron N8 can be inhibited at axon terminals AT11 by inhibitory neurotransmitter TRA and excited at axon terminals AT12 by an excitatory neurotransmitter TRB. Portions 27–29 are used to infuse an agonist of transmitter TRA, a reuptake blocker to transmitter TRA, a degrading enzyme blocker to transmitter TRA or an antagonist or degrading enzyme to transmitter TRB to raise the stimulation threshold of neurons N7–N9. Neurons N4–N6 are not affected by the infusion and can be selectively activated by simulation supplied by electrodes 38 and 40.

Figure 22:
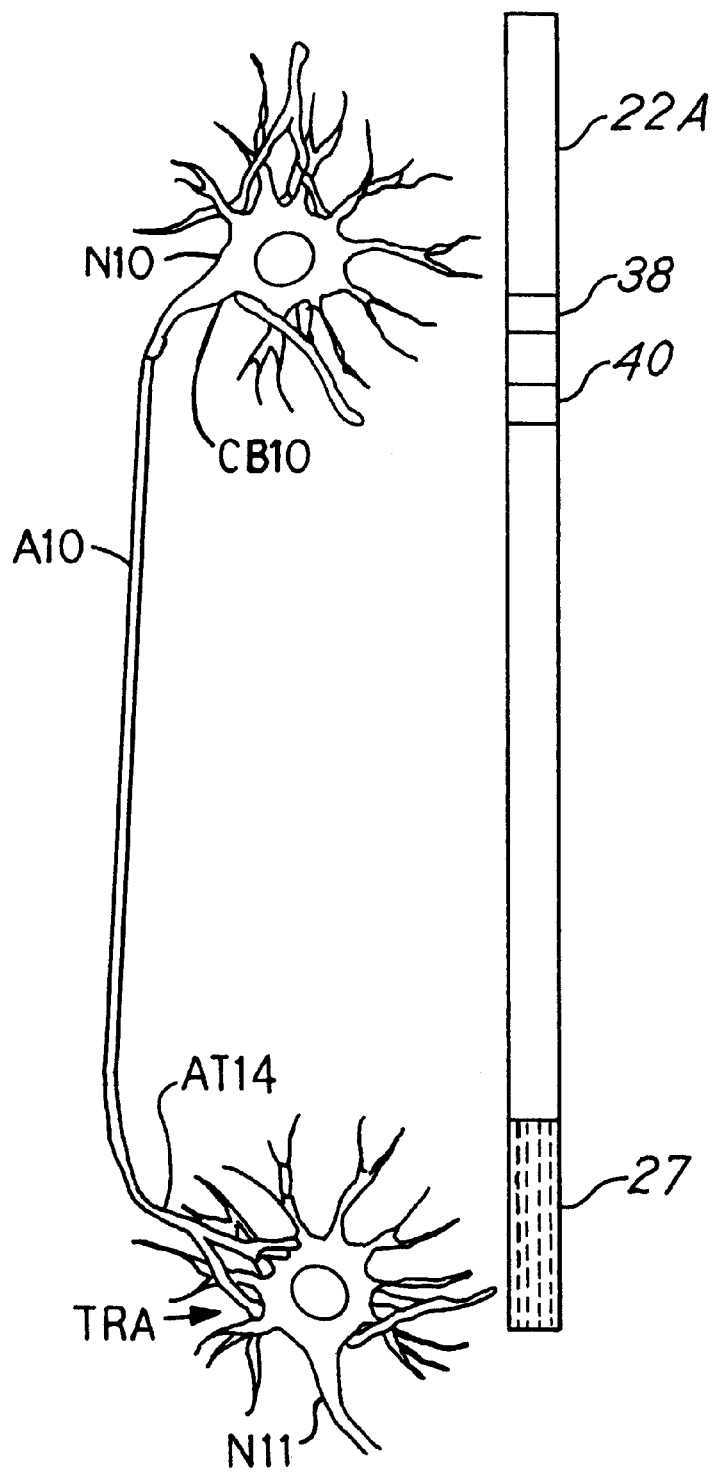

FIG. 22 illustrates a modified form of tube 22A in which infusion portion 27 is located more than 0.01 cm from electrodes 38 and 40 and infusion portions 28–29 have been removed. Neuron N10 has a cell body CB10 and an axon A10 that terminates in axon terminals AT14. A neuron N11 can be excited at axon terminals AT14 by an excitatory neurotransmitter TRA. Electrical stimulation of axon A10 causes the release of transmitter TRA at axon terminal AT14. Portion 27 is used to infuse an agent that blocks a degradative enzyme of transmitter TRA or an agent which blocks the reuptake of transmitter TRA. For each pulse administered by electrodes 38 and 40, the stimulation of neuron N11 is more potent. That is, more action potentials are generated in neuron N11.

Figure 23:
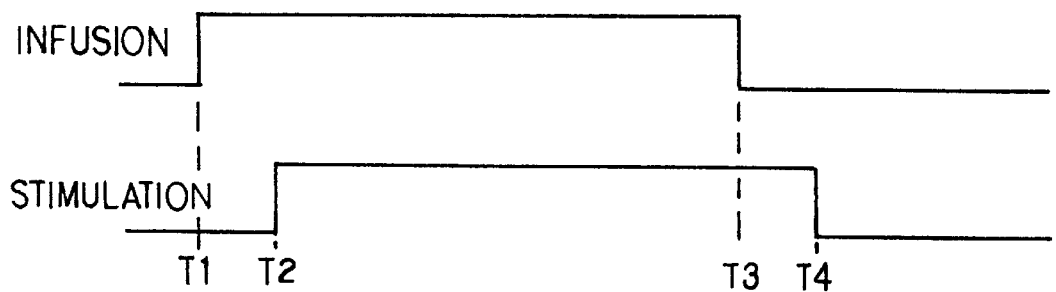
FIGS. 23–25 are timing diagrams showing the relationship between the administration of drugs and electrical stimulation to nerve tissue.

FIG. 23 illustrates various times at which infusion and stimulation can be applied by tube 22A. For example, infusion alone can be applied from time T1 to T2, infusion and stimulation can be both be applied from time T2 to T3, and stimulation alone can be applied from time T3 to T4. This regimen might be used in the case when selective activation of one neuronal population is desired. By beginning the infusion before beginning stimulation during time T1 to T2, the threshold for electrical activation of one population of neurons can be lowered or raised as needed. Another example would be if a precursor molecule, such as L-dopa, is infused to guard against depletion of the transmitter substance dopamine.

Figure 24:
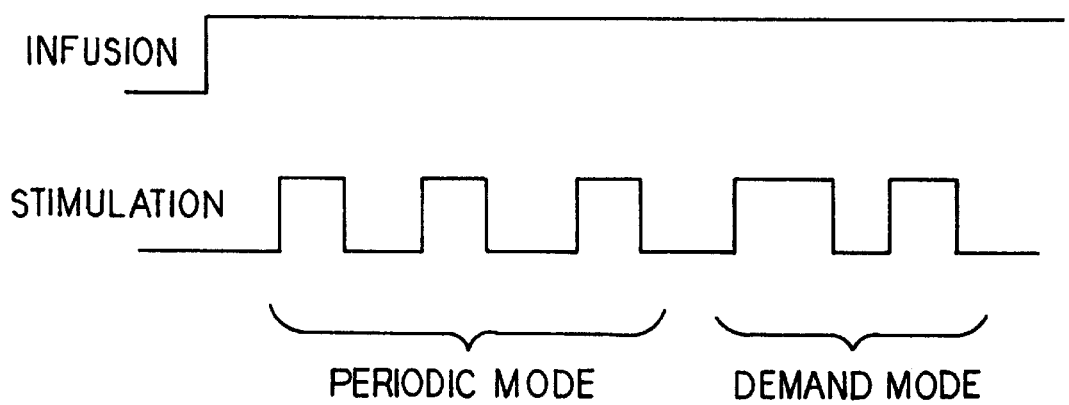
Figure 25:
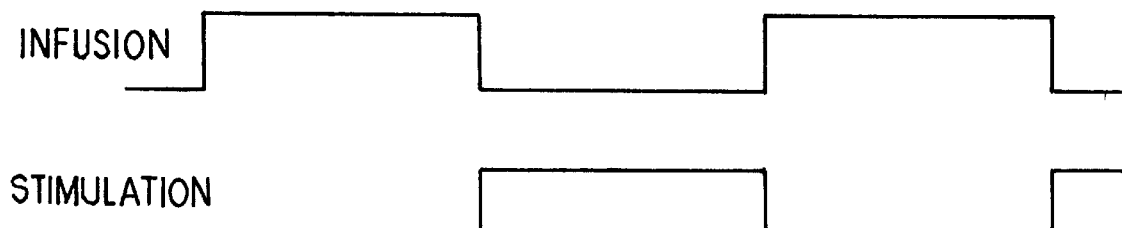

The stimulation might be applied periodically during the period of infusion either routinely or in response to sensor or patient generated demand as shown in FIG. 24. Alternatively, stimulation could be applied continuously with infusion occurring periodically. Patient activation of either infusion or stimulation may occur as a result of an increase in symptoms being experienced by the patient. Alternatively, the infusion of an agent to activate a neuronal population might be alternated with application of electrical stimulation of that same population, as shown in FIG. 25.

It also is possible to infuse an agent that has an affect upon the neuron population that is not strictly connected in time with the electrical depolarization of the neurons. In this case, the time of application of stimulation and infusion may be completely asynchronous. Or an agent could be infused that diffuses beyond the effects of the electrical stimulation but still has an advantageous effect on the brain independent of the stimulation effects.

In those instances where a continuous infusion of liquid agent is effective, the infusion device may be replaced with a static device such as is described in U.S. Pat. No. 4,892,538 (Aebischer et al.) which is incorporated by reference. An example of a static device is a device having a semipermeable wall enclosing encapsulated cells capable of secreting the appropriate agent. Alternatively, an implantable device could consist of a polymeric insert with the agent embedded within or on the surface of the polymer in such a way as to be slowly eluted from the polymer over time. Such a device is described in U.S. Pat. Nos. 4,346,709 (Schmitt) and 5,330,768 (Yamahira et al.), both of which are incorporated by reference. These alternative techniques could be employed with or without the simultaneous application of open-loop or closed-loop stimulation in the aforementioned manner.

By using the foregoing techniques, the number of AIMs experienced by persons with PD can be controlled with a degree of accuracy previously unattainable. Those skilled in the art will recognize that the preferred embodiment may be altered or amended without departing from the true spirit and scope of the invention, as defined in the accompanying claims.

We claim:

1. A therapeutic treatment method for reducing the occurrence of abnormal involuntary movements by means of an implantable pump and a catheter having a proximal end coupled to the pump and a discharge portion for infusing therapeutic dosages of at least one drug, as well as a signal generator and at least one implantable electrode having a proximal end and a stimulation portion, the method comprising the steps of:

(a) implanting at least one electrode so that the stimulation portion lies in communication with a first predetermined site in a brain;

(b) implanting the catheter so that the discharge portion lies in communication with a second predetermined site in the brain;

(c) coupling the proximal end of the implanted electrode to the signal generator;

(d) coupling the catheter to the pump; and (e) operating the signal generator and pump to block or reduce activity of a Centremedian-Parafasicularis nucleus in the brain by delivering electrical stimulation to the first predetermined site and at least one drug to the second predetermined site.

2. A method, as claimed in claim 1, further comprising the steps of:

(f) positioning a sensor at a third predetermined site of a body;

(g) sensing the extent of the abnormal involuntary movements;

(h) generating a sensor signal indicating the extent of the abnormal involuntary movements; and (i) regulating the operation of the signal generator and the pump in response to the sensor signal to treat or reduce the abnormal involuntary movements.

3. A method, as claimed in claim 2, wherein said step of sensing includes the step of detecting changes in electromagnetic waves generated by muscle or nerve tissue.

4. A method, as claimed in claim 2, wherein said step of regulating comprises the step of executing a control algorithm to regulate the operation of the signal generator and the pump.

5. A method, as claimed in claim 4, wherein said step of sensing includes the step of communicating by telemetry the extent of the abnormal involuntary movements for use by the control algorithm.

6. A method, as claimed in claim 1, flier comprising the step of (f) delivering electrical stimulation to a first determined site; and (g) delivering drug the to a second predetermined site.

7. A method as claimed in claim 6, wherein steps (f) and (g) are achieved using a combined electrode-catheter.

8. A method, as claimed in claim 1, wherein the first predetermined site is selected from the group consisting of Centremedian-parafasicularis nucleus of the thalamus (CM-Pf complex), ventrolateral thalamus (Thal), substantia nigra pars reticulata (SNr), subthalamic nucleus (STN), external segment of globus pallidus (GPe) and neostriatum, and wherein said stimulation and said discharge are selected to reduce thalamic output.

9. A method, as claimed in claim 1, wherein the second predetermined site is selected from the group consisting of Centremedian-parafasicularis nucleus of the thalamus (CM-Pf complex), ventrolateral thalamus (Thal), substantia nigra pars reticulata (SNr), subthalamic nucleus (STN), external segment of globus pallidus (GPe) and neostriatum, and wherein said stimulation and said discharge are selected to reduce thalamic output.

10. A method, as claimed in claim 1, wherein the step of operating includes the step of operating the signal generator and pump to block or reduce activity in an internal segment of globus pallidus (GPi) by delivering electrical stimulation to the first predetermined site and at least one drug to the second predetermined site.

11. A method, as claimed in claim 1, wherein said step of operating includes the step of operating the signal generator to pulse at a repetition rate of 2 to at least 2500 Hz.

12. A method, as claimed in claim 1, wherein the step of operating includes the step of delivering to the brain at least one drug selected from the group consisting of an anesthetic, a GABA agonist, a GABA antagonist, a glutamate antagonist, a glutamate agonist, a degrading enzyme, a reputake blocker, and a dopamine antagonist.

13. A method, as claimed in claim 1, wherein the brain comprises a first neural tissue responsive to a first type of neurotransmitter and a second neural tissue responsive to a second type of neurotransmitter, and wherein the step of operating includes the step of selecting at least one drug to act on the first and second type of neurotransmitter so that the stimulation required to create an action potential in the neural tissue is reduced compared to the stimulation required to create an action potential in the second neural tissue.

14. A method, as claimed in claim 1, wherein the brain comprises a first neural tissue responsive to a first type of neurotransmitter and a second neural tissue comprising fibers of passage, and wherein the step of operating includes the step of selecting at least one drug to act on the first neural tissue so that the stimulation required to create an action potential in the first neural tissue is raised, whereby said fibers of passage can be stimulated without creating action potentials in the first neural tissue.

15. A method, as claimed in claim 1, wherein the brain comprises a first nerve comprising an axon that terminates in axon terminals and a second nerve comprising a cell body including a receiving cell that communicates with the axon terminals across a synapse by means of a neurotransmitter, wherein the step of implanting the electrode includes that step of positioning the electrode so that the stimulation site is in communication within the axon and wherein the step of implanting the includes the step of positioning so that the infusion site is in communication with the synapse, whereby the stimulation of the axon results in increased excitment of the second nerve.

16. A therapeutic treatment method for reducing the occurrence of abnomal involuntary movements by means of a signal generator and at least one implantable electrode having a proximal end and a stimulation portion, the method comprising the steps of:

(a) implanting at least one electrode so that the stimulation portion lies in communication with a predetermined site in a brain;

(b) coupling the proximal end of the implanted electrode to the signal generator;

(c) operating the signal generator to block activity of a Centremedian-Parafasicularis nucleus in the brain.

17. A method, as claimed in claim 16, wherein the step of operating includes the step of selecting amplitude, width and frequency of stimulation by the electrode.

18. A method, as claimed in claim 16, further comprising the steps of:

(f) sensing the extent of the abnormal involuntary movements and generating a sensor signal; and (g) regulating the operation of the electrode in response to the sensor signal.

19. A method, as claimed in claim 18, wherein the step of sensing includes the step of sensing a physiological symptom of the abnormal involuntary movement.

20. A method, as claimed in claim 18, wherein the step of regulating includes the step of adjusting a parameter of the stimulation, the parameter being selected from the group consisting of amplitude, width and frequency.

21. A method, as claimed in claim 20, further comprising the step of readjusting over time at least one parameter of the stimulation downward to decease the effects of the stimulation.

22. A method, as claimed in claim 16, wherein the predetermined site is selected from the group consisting of Centremedian-parafasicularis nucleus of the thalamus (CM-Pf complex), ventrolateral thalamus (Thal), substantia nigra pars reticulata (SNr), subthalamic nucleus (STN), external segment of globus pallidus (GPe) and neostriatum, and wherein said stimulation and said discharge are selected to reduce thalamic output.

23. A method, as claimed in claim 16, wherein the step of operating includes the step of blocking activity in an internal segment of globus pallidus (GPi).

24. A method, as claimed in claim 16, wherein the step of operating includes the step of operating the signal generator to pulse at a repetition rate of 10–2500 Hertz.

25. A therapeutic treatment method for reducing the occurrence of abnormal involuntary movements by means of an implantable pump and a catheter having a proximal end coupled to the pump and a discharge portion for infusing therapeutic dosages of at least one drug, the method comprising the steps of:

(a) implanting the catheter so that the discharge portion lies in communication with a predetermined site in the brain;
   (b) coupling the catheter to the pump;
   (c) operating the pump to block or reduce activity of a Centremedian-Parafasicularis nucleus in the brain by delivering at least one drug to the predetermined site.

26. A method, as claimed in claim 25, wherein the step of operating includes the step of selecting a drug dosage.

27. A method, as claimed in claim 26, wherein the step of operating includes the step of selecting a time interval for drug delivery.

28. A method, as claimed in claim 25, further comprising the steps of:

(d) positioning a sensor at a third predetermined site of a body;
   (e) sensing the extent of the abnormal involuntary movements;
   (f) generating a sensor signal indicating the extent of the abnormal involuntary movements; and
   (g) regulating the operation of the pump in response to the sensor signal to treat or reduce the abnormal involuntary movements.

29. A method, as claimed in claim 28, wherein the step of regulating includes the step of adjusting drug dosage and time interval for drug delivery.

30. A method, as claimed in claim 25, wherein the predetermined site is selected from the group consisting of Centramedian-Parafascularis nucleus of the thalamus (CM-Pf complex), ventrolateral thalamus (Thal), substantia nigra pars reticulata (SNr), subthalamic nucleus (STN), external segment of globus pallidus (GPe) and neostriatum, and wherein said stimulation and said discharge are selected to reduce thalamic output.

31. A method, as claimed in claim 25, wherein the step of operating includes the step of operating the pump to block or reduce activity in an internal segment of globus pallidus (GPi) by delivering at least one drug to the predetermined site.

32. A method, as claimed in claim 25, further comprising the steps of:

(d) implanting a second catheter to discharge a second drug to a second predetermined site in the brain;
   (e) coupling the second catheter to a second pump; and
   (f) operating the second pump to block or reduce activity of the Centremedian-Parafasicularis nucleus in the brain by delivering the second drug to the second predetermined site.

33. A therapeutic treatment method for reducing the occurrence of abnormal involuntary movements by means of an implantable pump and a catheter having a proximal end coupled to the pump and a discharge portion for infusing therapeutic dosages of at least one drug, as well as a signal generator and at least one implantable electrode having a proximal end and a stimulation portion, the method comprising the steps of:

(a) implanting at least one electrode so that the stimulation portion lies in communication with a first predetermined site in a brain;
   (b) implanting the catheter so that the discharge portion lies in communication with a second predetermined site in the brain;
   (c) coupling the proximal end of the implanted electrode to the signal generator;
   (d) coupling the catheter to the pump;
   (e) detecting the extent of the abnormal involuntary movements or the extent of a symptom of the abnormal involuntary movements;
   (f) operating the signal generator and pump to block or reduce activity of a Centremedian-Parafasicularis nucleus in the brain by delivering electrical stimulation to the first predetermined site and at least one drug to the second predetermined site, whereby the abnormal involuntary movements are treated or reduced.

34. A method, as claimed in claim 33, wherein the first predetermined site overlaps with the second predetermined site.

35. A therapeutic treatment method for reducing the occurrence of abnormal involuntary movements by means of an implantable pump and a catheter having a proximal end coupled to the pump and a discharge portion for infusing therapeutic dosages of at least one drug, the method comprising the steps of:

(a) implanting the catheter so that the discharge portion lies in communication with a predetermined site in the brain;
   (b) coupling the catheter to the pump;
   (c) detecting the extent of the abnormal involuntary movements or the extent of a symptom of the abnormal involuntary movements;
   (d) operating the pump to block or reduce activity of a Centremedian-Parafasicularis nucleus in the brain by delivering at least one drug to the predetermined site, whereby the abnormal involuntary movements are treated or reduced.

36. A method, as claimed in claim 1, wherein the first predetermined site overlaps with the second predetermined site.

* * * * *

UNITED STATES PATENT AND TRADEMARK OFFICE
CERTIFICATE OF CORRECTION

PATENT NO. : 6,227,203 B1
DATED : May 8, 2001
INVENTOR(S) : Rise et al.

Page 1 of 1

It is certified that error appears in the above-identified patent and that said Letters Patent is hereby corrected as shown below:

Column 17, claim 6,
Line 34, "drug the to" should read -- drug therapy to --

Column 18, claim 15,
Line 27, "the includes" should read -- the catheter includes --

Column 19, claim 30,
Line 45, "Centramedian-Parafascularis" should read -- Centremedian-Parafasicularis --

Signed and Sealed this

Eighth Day of January, 2002

Attest:

JAMES E. ROGAN
Attesting Officer
Director of the United States Patent and Trademark Office